(12) United States Patent
Wardle et al.

(10) Patent No.: US 9,579,234 B2
(45) Date of Patent: Feb. 28, 2017

(54) OCULAR IMPLANT SYSTEM AND METHOD

(71) Applicant: Ivantis, Inc., Irvine, CA (US)

(72) Inventors: John Wardle, San Clemente, CA (US); Andrew T. Schieber, Irvine, CA (US); Kenneth M. Galt, Laguna Hills, CA (US)

(73) Assignee: IVANTIS, INC., Irvine, CA (US)

( * ) Notice: Subject to any disclaimer, the term of this patent is extended or adjusted under 35 U.S.C. 154(b) by 302 days.

(21) Appl. No.: 14/279,983

(22) Filed: May 16, 2014

(65) Prior Publication Data

US 2014/0249463 A1 Sep. 4, 2014

Related U.S. Application Data

(62) Division of application No. 12/911,451, filed on Oct. 25, 2010, now abandoned.

(60) Provisional application No. 61/254,523, filed on Oct. 23, 2009.

(51) Int. Cl.
*A61F 9/007* (2006.01)

(52) U.S. Cl.
CPC .............................. *A61F 9/00781* (2013.01)

(58) Field of Classification Search
CPC .... A61F 9/0017; A61F 9/007; A61F 9/00781; A61K 9/0051; A61M 27/002
See application file for complete search history.

(56) References Cited

U.S. PATENT DOCUMENTS

| | | |
|---|---|---|
| 703,296 A | 6/1902 | Arnold |
| 1,601,709 A | 10/1926 | Windom |
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,601,713 A | 7/1986 | Fuquo |
| 4,689,040 A | 8/1987 | Thompson |
| 4,699,140 A | 10/1987 | Holmes et al. |
| 4,706,669 A | 11/1987 | Schlegel |
| 4,722,724 A | 2/1988 | Schocket |
| 4,733,665 A | 3/1988 | Palmaz |

(Continued)

FOREIGN PATENT DOCUMENTS

| | | |
|---|---|---|
| AU | 1998/76197 B2 | 2/1999 |
| CN | 1950091 A | 4/2007 |

(Continued)

OTHER PUBLICATIONS

Schieber et al.; U.S. Appl. No. 14/843,563 entitled "Ocular implants for delivery into the eye," filed Sep. 2, 2015.

(Continued)

*Primary Examiner* — Julie A Szpira
(74) *Attorney, Agent, or Firm* — Shay Glenn LLP

(57) ABSTRACT

A method of treating glaucoma in a human eye by inserting a distal exit port of a cannula at least partially into Schlemm's canal of the eye; delivering a dye through the cannula into Schlemm's canal; identifying obstructions within Schlemm's canal; and delivering an ocular implant through the cannula into Schlemm's canal.

20 Claims, 26 Drawing Sheets

(56) References Cited

U.S. PATENT DOCUMENTS

| | | |
|---|---|---|
| 4,750,901 A | 6/1988 | Molteno |
| 4,826,478 A | 5/1989 | Schocket |
| 4,861,341 A | 8/1989 | Woodburn |
| 4,880,000 A | 11/1989 | Holmes et al. |
| 4,886,488 A | 12/1989 | White |
| 4,919,130 A | 4/1990 | Stoy et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,290,267 A | 3/1994 | Zimmermann |
| 5,360,399 A | 11/1994 | Stegmann |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,536,259 A | 7/1996 | Utterberg |
| 5,575,780 A | 11/1996 | Saito |
| 5,591,223 A | 1/1997 | Lock et al. |
| 5,613,972 A | 3/1997 | Lee et al. |
| 5,626,558 A | 5/1997 | Suson |
| 5,653,753 A | 8/1997 | Brady et al. |
| 5,676,669 A | 10/1997 | Colvard |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,919,171 A | 7/1999 | Kira et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 * | 6/2001 | Cozean .................. A61F 9/008 606/15 |
| D444,874 S | 7/2001 | Haffner et al. |
| 6,328,747 B1 | 12/2001 | Nun |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 * | 9/2005 | Brown .................. A61B 3/101 600/309 |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B1 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 * | 2/2009 | Haffner .............. A61F 9/00781 604/521 |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,512,404 B2 | 8/2013 | Frion et al. |
| 8,529,494 B2 | 9/2013 | Euteneuer et al. |
| 8,551,166 B2 | 10/2013 | Schieber et al. |
| 8,636,647 B2 | 1/2014 | Silvestrini et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Scheiber et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 * | 1/2002 | Berlin ................ A61F 9/00802 606/4 |
| 2002/0052653 A1 | 5/2002 | Durgin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0193805 A1 | 12/2002 | Ott et al. |
| 2003/0004457 A1 | 1/2003 | Andersson |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0082939 A1 | 4/2004 | Berlin |
| 2004/0088048 A1 | 5/2004 | Richter et al. |
| 2004/0098124 A1 | 5/2004 | Freeman et al. |

(56) References Cited

U.S. PATENT DOCUMENTS

| | | |
|---|---|---|
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1* | 11/2005 | Tu ................... A61F 9/00781 514/252.16 |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1* | 10/2006 | Tu ................... A61F 9/00781 623/4.1 |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1* | 4/2007 | Solovay ............. A61F 9/00781 623/4.1 |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0135681 A1 | 6/2007 | Chin et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0219509 A1 | 9/2007 | Tashiro et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1* | 9/2008 | Burns ................. A61F 9/00781 604/9 |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1* | 1/2009 | Yamamoto ........... A61K 31/728 424/489 |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0132040 A1* | 5/2009 | Frion ................. A61F 9/00781 623/6.12 |
| 2009/0138081 A1 | 5/2009 | Bergheim et al. |
| 2009/0182421 A1* | 7/2009 | Silvestrini .......... A61F 9/00781 623/6.13 |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2013/0150959 A1 | 6/2013 | Schieber et al. |
| 2013/0172804 A1 | 7/2013 | Schieber et al. |
| 2013/0182223 A1 | 7/2013 | Wardle et al. |
| 2013/0231603 A1 | 9/2013 | Wardle et al. |
| 2013/0267887 A1 | 10/2013 | Kahook et al. |
| 2013/0281907 A1 | 10/2013 | Wardle et al. |
| 2013/0331761 A1 | 12/2013 | Euteneuer et al. |
| 2014/0066821 A1 | 3/2014 | Freidland et al. |
| 2014/0066831 A1 | 3/2014 | Silvestrini et al. |

(56) References Cited

U.S. PATENT DOCUMENTS

| | | | |
|---|---|---|---|
| 2014/0114229 | A1 | 4/2014 | Wardle et al. |
| 2014/0121584 | A1 | 5/2014 | Wardle et al. |
| 2014/0214161 | A1 | 7/2014 | Schieber et al. |
| 2014/0323944 | A1 | 10/2014 | Scheiber et al. |
| 2015/0250649 | A1 | 9/2015 | Euteneuer et al. |
| 2016/0051406 | A1 | 2/2016 | Wardle et al. |

FOREIGN PATENT DOCUMENTS

| | | |
|---|---|---|
| DE | 4226476 C1 | 8/1993 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2002542872 | 12/2002 |
| JP | 2006517848 | 8/2006 |
| JP | 2006289075 A | 10/2006 |
| JP | 2010509003 | 3/2010 |
| JP | 2011502649 | 1/2011 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |
| WO | WO 2011/053512 A1 | 5/2011 |
| WO | WO 2011/057283 A1 | 5/2011 |
| WO | WO 2011/106781 A1 | 9/2011 |
| WO | WO 2011/150045 A1 | 12/2011 |
| WO | WO 2012/051575 A2 | 4/2012 |

OTHER PUBLICATIONS

Wardle et al.; U.S. Appl. No. 14/363,409 entitled "Delivering ocular implants into the eye," filed Jun. 6, 2014.
Wardle et al.; U.S. Appl. No. 14/592,703 entitled "Delivering ocular implants into the eye," filed Jan. 8, 2015.
Schieber et al.; U.S. Appl. No. 14/691,267 entitled "Ocular implants with asymmetric flexibility," filed Apr. 20, 2015.
Schieber et al.; U.S. Appl. No. 14/692,442 entitled "Methods and apparatus for delivering ocular implants into the eye," filed Apr. 21, 2015.
Schieber et al.; U.S. Appl. No. 14/693,582 entitled "Methods and apparatus for delivering ocular implants into the eye," filed Apr. 22, 2015.
Schiber et al.; U.S. Appl. No. 14/440,610 entitled "Apparatus for delivering ocular implants into an anterior chamber of the eye," filed May 5, 2015.
Bahler, et al.; Trabecular bypass stents decrease intraocular pressure in cultured human anterior segments; Amer. Journal of Ophthalmology; vol. 138, No. 6; pp. 988-994.e2; Dec. 2004.
D'Ermo, et al.; Our results with the operation of ab externo trabeculotomy; Ophthalmologica; vol. 163; pp. 347-355; Feb. 1971.
Ellingsen et al.; Trabeculotomy and sinusotomy in enucleated human eyes; Investigative Ophthalmology; vol. 11; pp. 21-28; Jan. 1972.
Grant; Experimental aqueous perfusion in enucleated human eyes; Archives of Ophthalmology; vol. 69; pp. 783-801; Jun. 1963.
Johnstone et al.; "Microsurgery of Schlemm's Canal and the Human Aqueous Outflow System;" American Journal of Ophthalmology, vol. 76 (6): 906-917; Dec. 1973.
Lee et al.; Aqueous-venous shunt and intraocular pressure. Preliminary report of animal studies; Investigative Ophthalmology; vol. 5; No. 1; pp. 59-64; Feb. 1966.
Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.
Moses, Robert; The effect of intraocular pressure on resistance to outflow; Survey of Ophthalmology; vol. 22; No. 2; pp. 88-100; Sep.-Oct. 1977.
Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Schieber et al.; U.S. Appl. No. 15/012,544 entitled "Methods and devices for increasing aqueous humor outflow," filed Feb. 1, 2016.
Wardle et al.; U.S. Appl. No. 15/150,175 entitled "Ocular implants for delivery into an anterior chamber of the eye," filed May 9, 2016.

\* cited by examiner

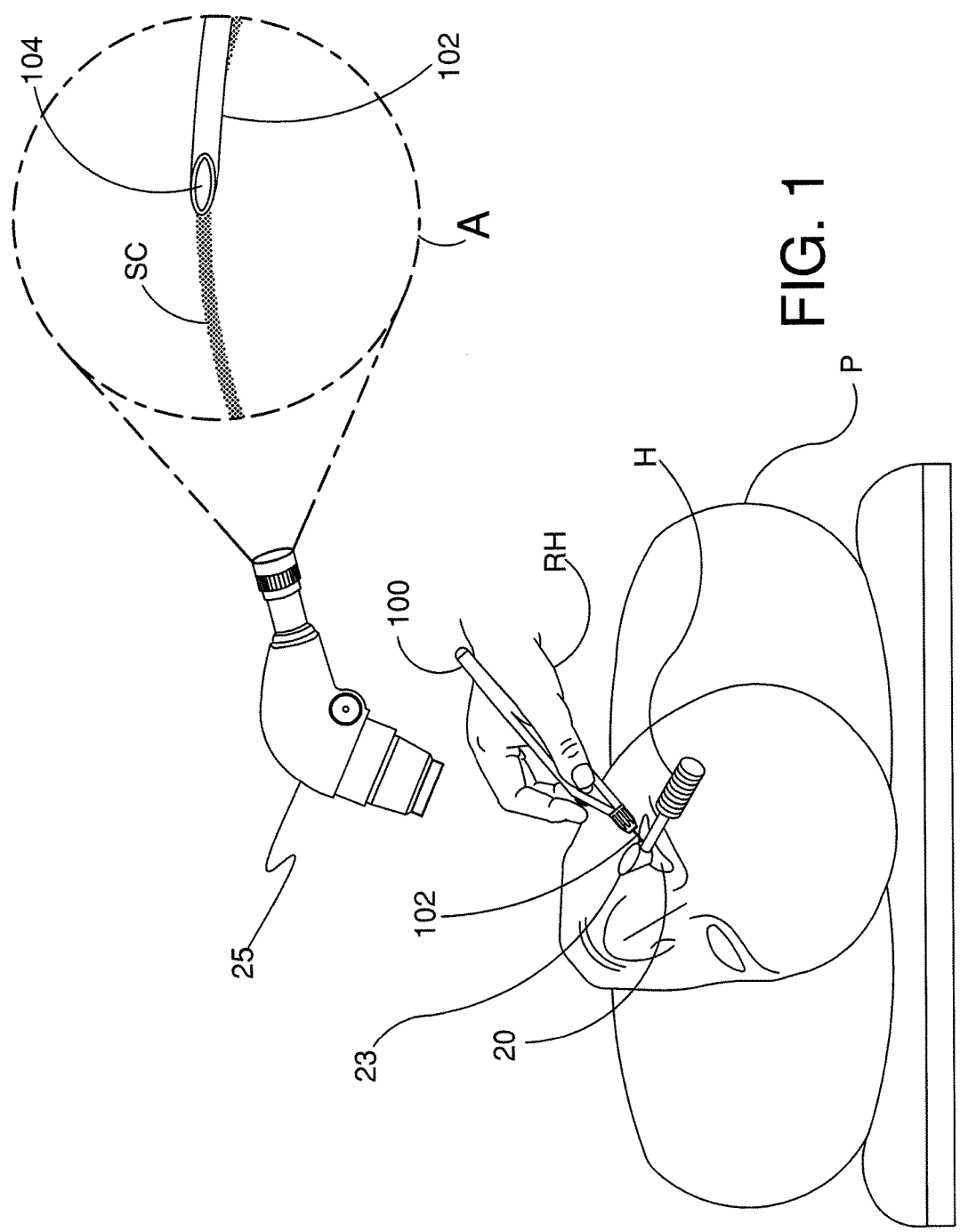

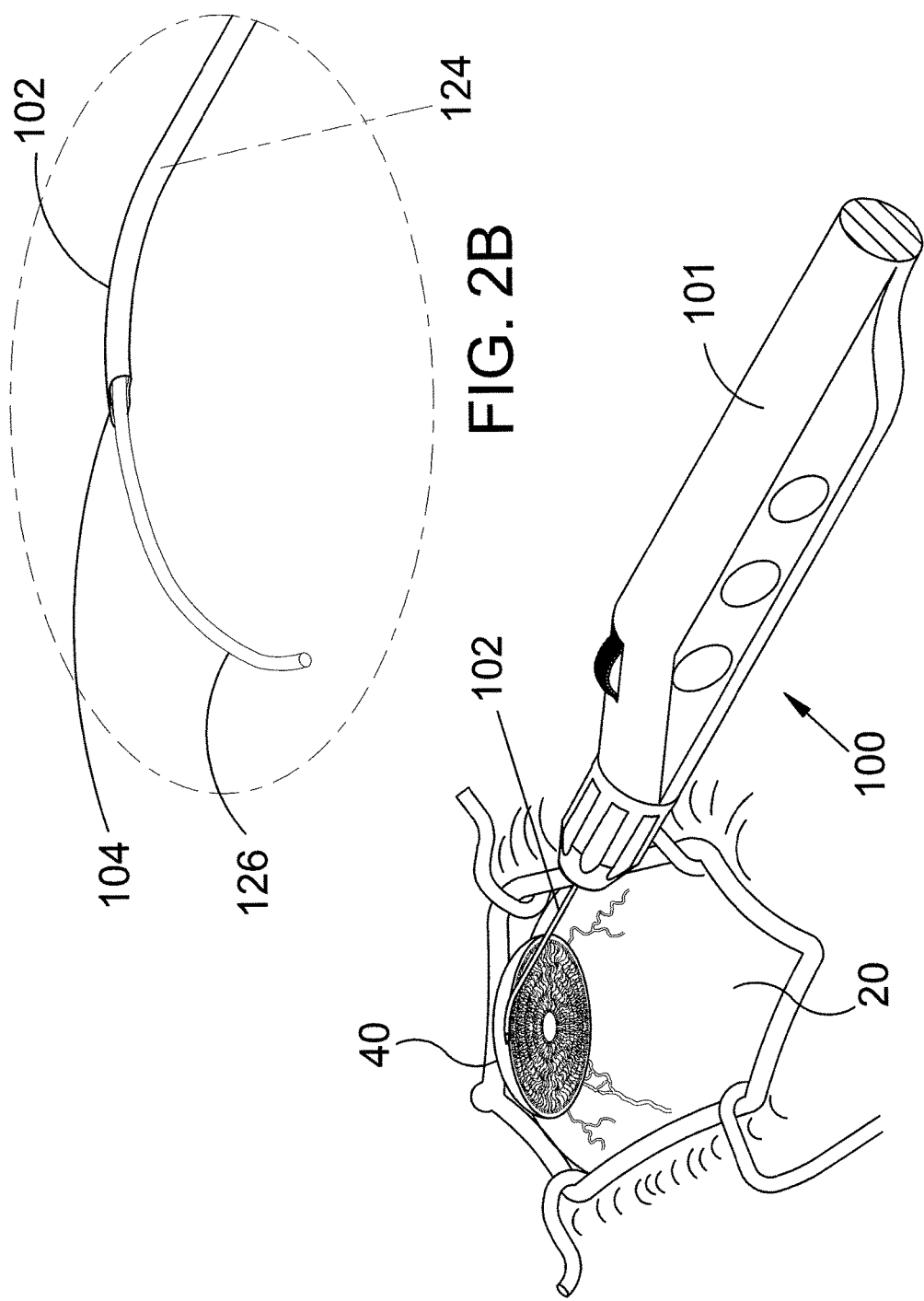

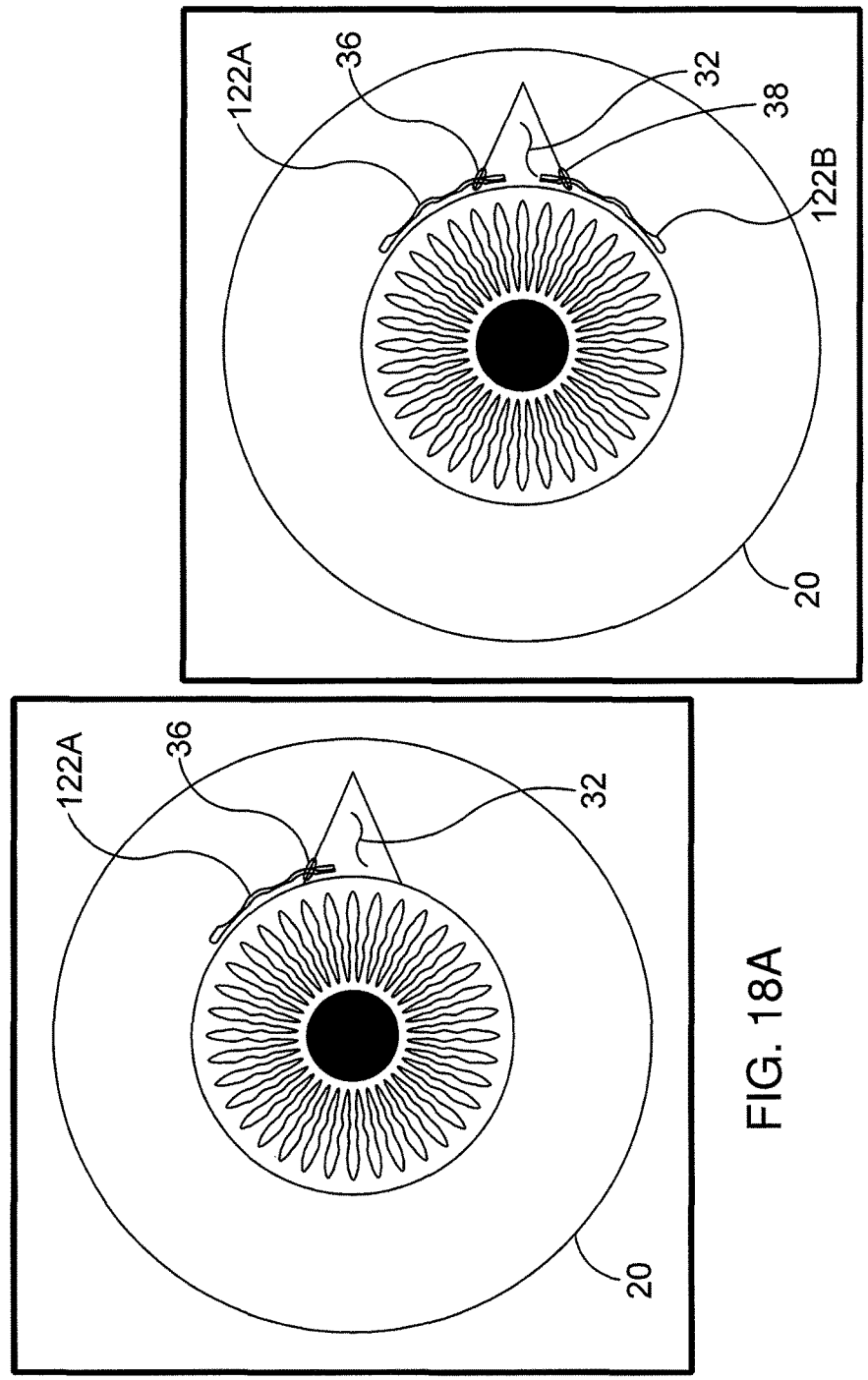

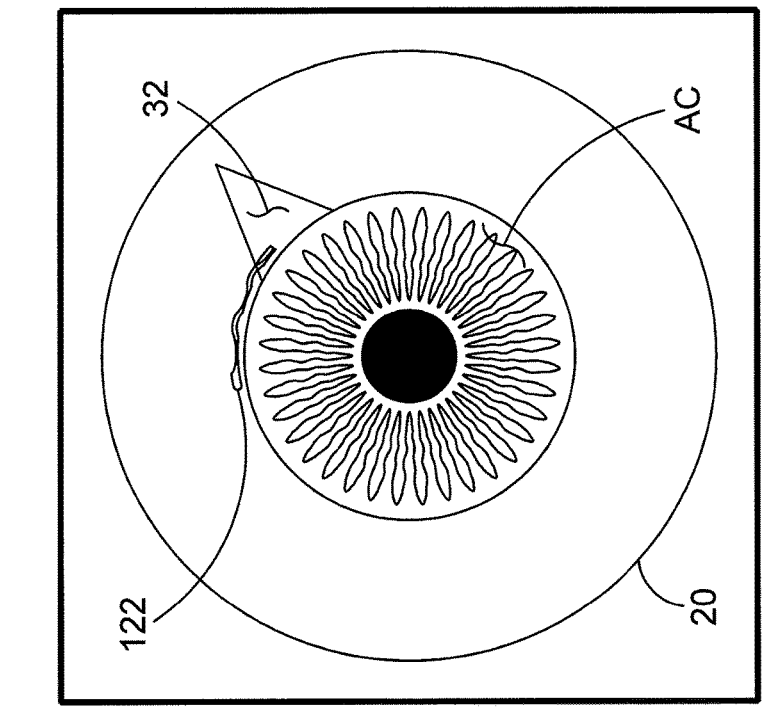
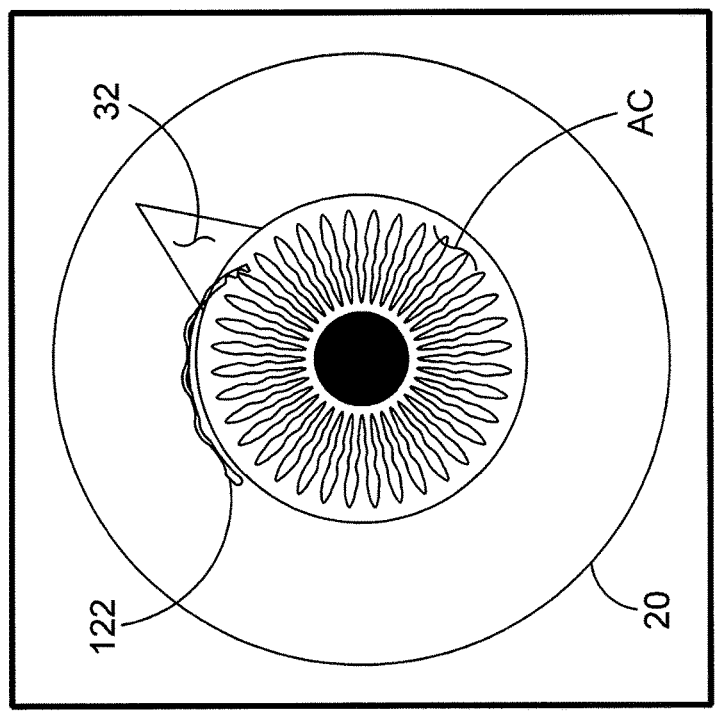
FIG. 19B
FIG. 19A

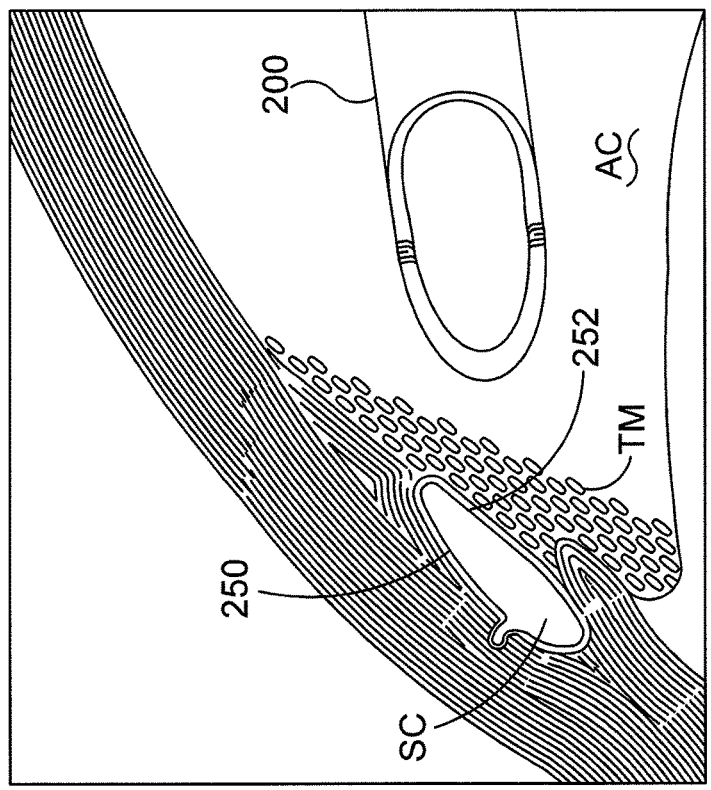
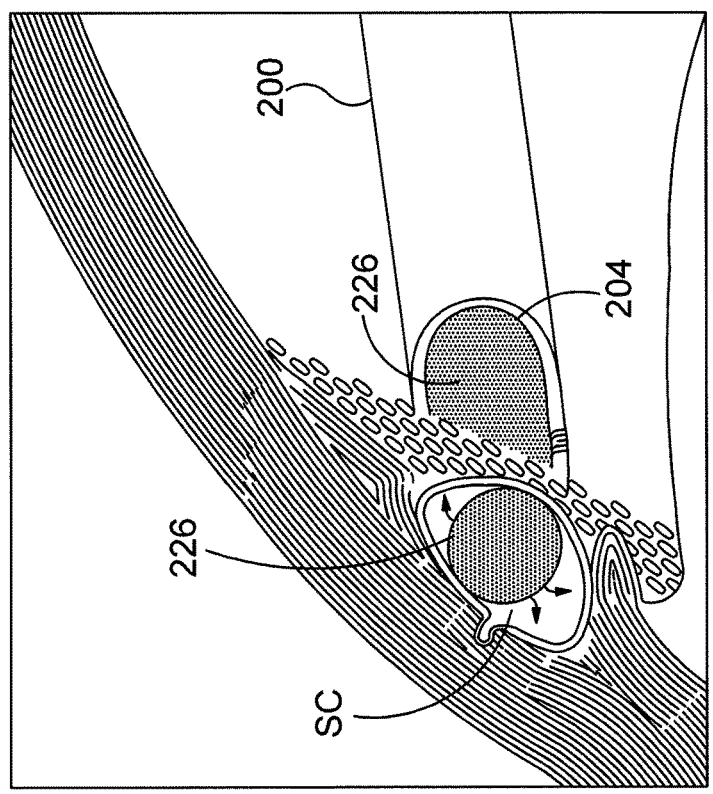
FIG. 20C
FIG. 20D

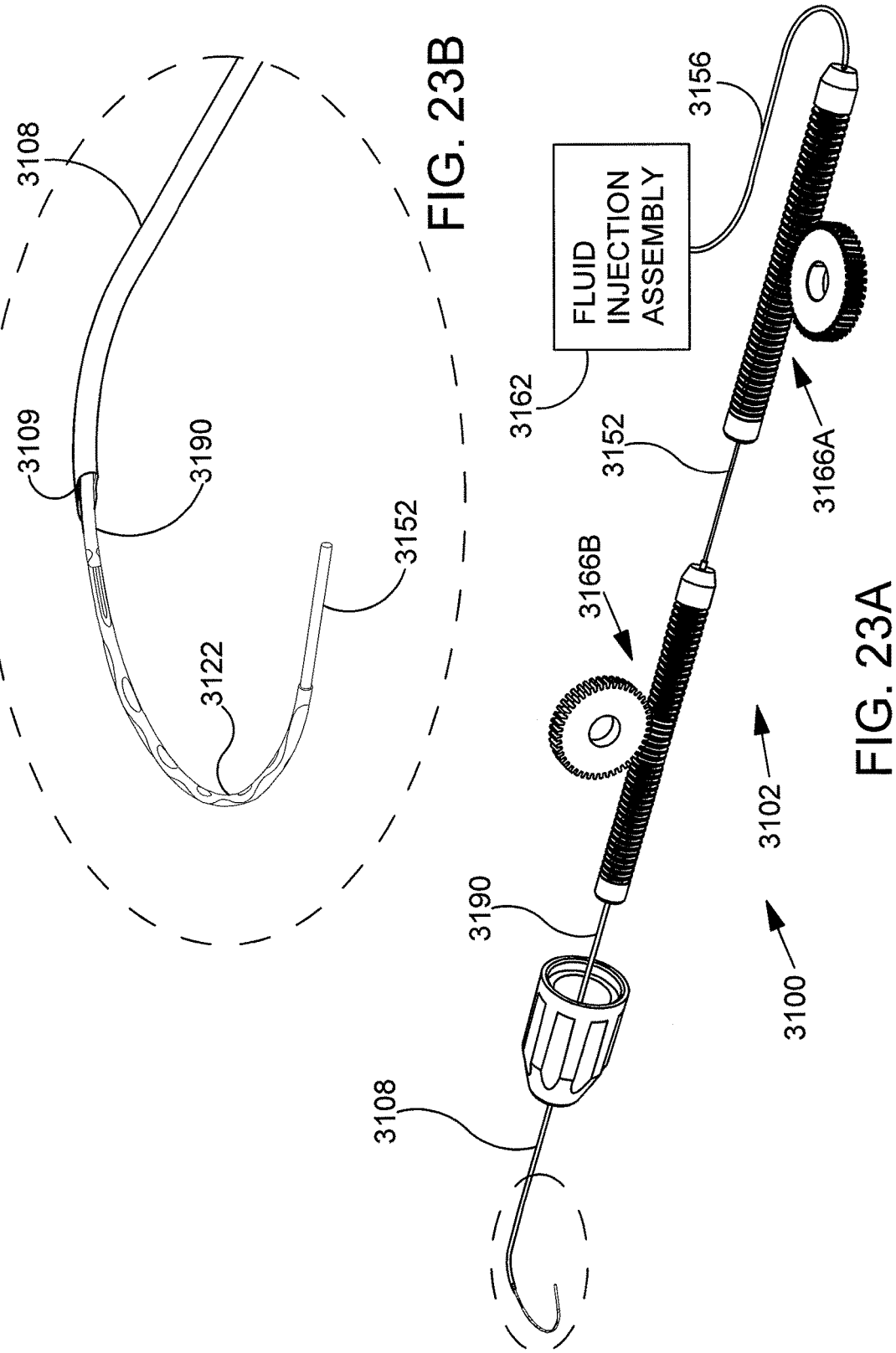

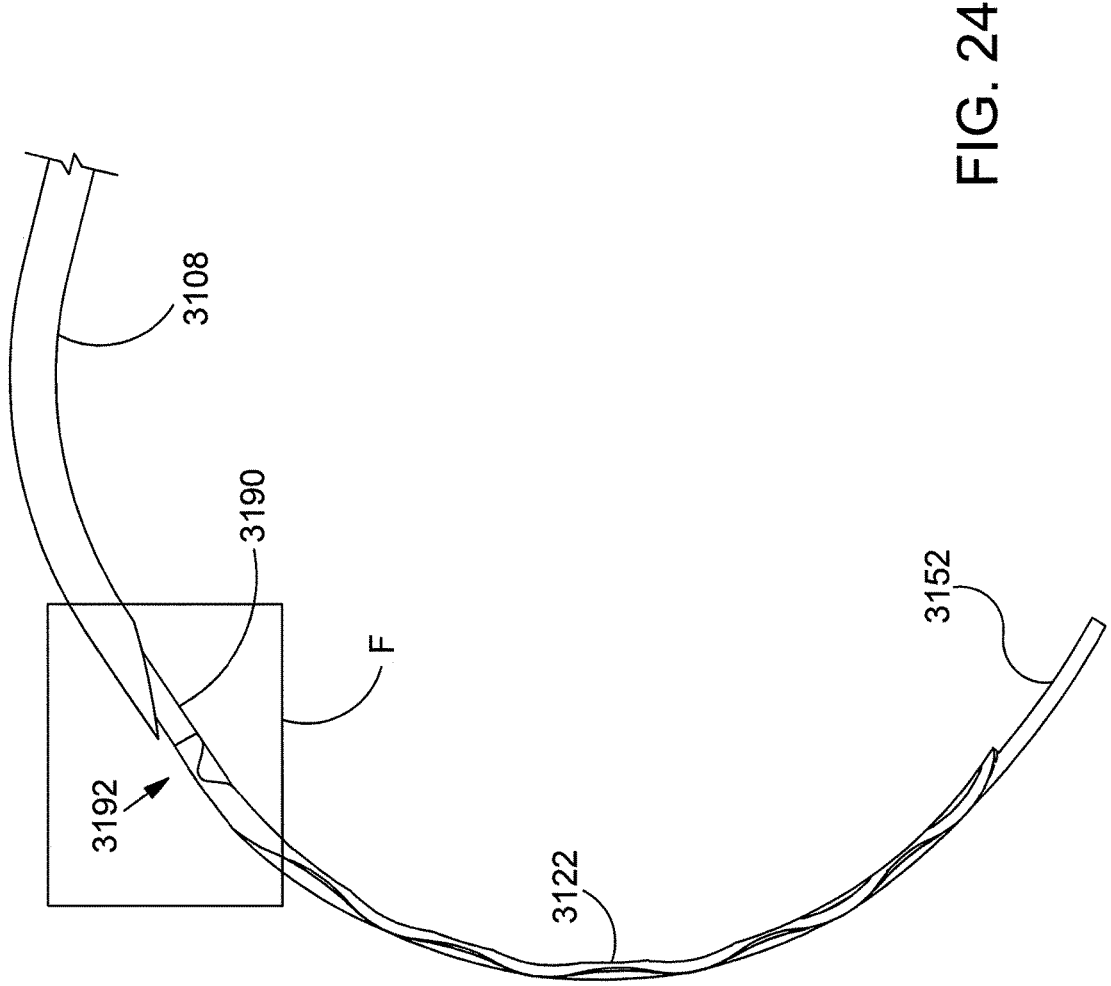

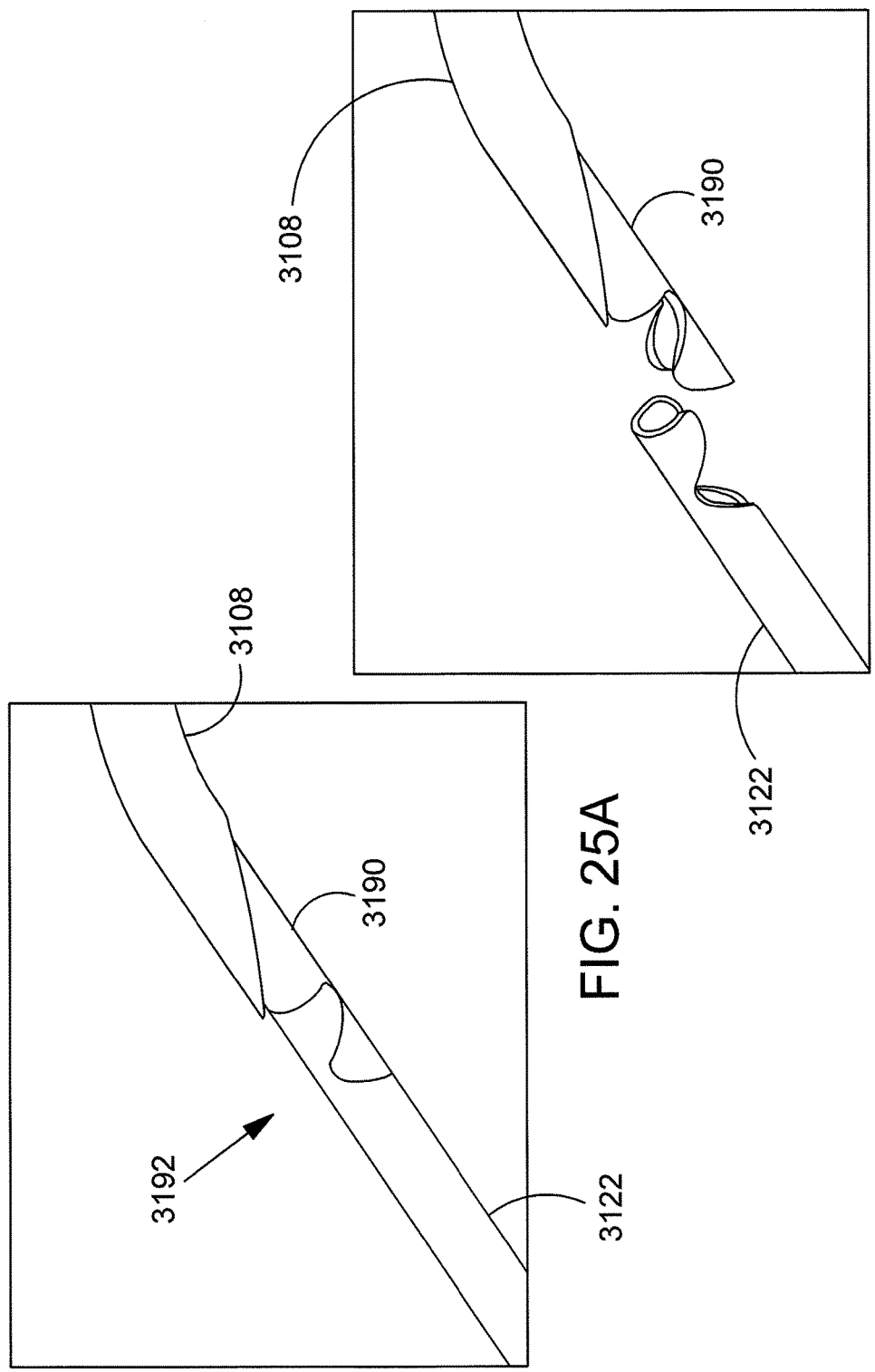

OCULAR IMPLANT SYSTEM AND METHOD

CROSS REFERENCE TO RELATED APPLICATIONS

This application is a divisional of U.S. patent application Ser. No. 12/911,451, filed Oct. 25, 2010 which claims the benefit under 35 U.S.C. §119 of U.S. Provisional Application No. 61/254,523, filed Oct. 23, 2009, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma.

In addition to drug treatments, a variety of surgical treatments for glaucoma have been described. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a sub-conjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. No. 6,450,984; U.S. Pat. No. 6,450,984).

More recently, glaucoma treatment devices that are disposed partially or completely within Schlemm's canal have been described. Examples of such devices may be found, e.g., in U.S. Pat. No. 7,740,604; U.S. Patent Publ. No. 2009/0082860; U.S. Patent Publ. No. 2009/0227934; U.S. Patent Publ. No. 2009/0132040; U.S. Patent Publ. No. 2010/0121342; U.S. Patent Publ. No. 2006/0195187; and U.S. application Ser. No. 12/833,863.

SUMMARY OF THE INVENTION

In some cases, the Schlemm's canal of a patient suffering from glaucoma has lost some or all of its natural functionality. Due to the abnormal pressures caused by glaucoma, Schlemm's canal and related tissues may have lost the ability to move. In some patients, these conditions may result in the collapse and subsequent closure of part or all of Schlemm's canal. When this is the case, portions of the wall of Schlemm's canal may be pushed closed and may not be allowed to rebound to an open shape. Over time, the collapsed wall of Schlemm's canal may adhere to itself causing the canal to become compartmentalized. Prior to implantation of an implant into Schlemm's canal, therefore, it may be advantageous to determine whether the lumen of Schlemm's canal is partially or completely blocked, i.e., to establish and confirm that enough space exists for an implant to reside and optionally to open up part of all of the canal lumen.

One aspect of the invention provides an ocular implant and delivery system having a channel tool (such as a torque tube or coil) adapted to extend through at least a portion of Schlemm's canal of a human eye and to determine whether the Schlemm's canal portion provides a suitable location for the delivery of an ocular implant; an ocular implant adapted to be disposed within Schlemm's canal of a human eye; and a cannula comprising a distal opening adapted to deliver the channel tool and the ocular implant into Schlemm's canal of the eye. In some embodiments, the channel tool is further adapted to open a channel within the Schlemm's canal portion.

Some embodiments of the invention also have a proximal control adapted to be operated from exterior to the eye to move the channel opening tool and the ocular implant when the distal opening of the cannula is within the eye. The channel opening tool may be configured to be disposed within the ocular implant and to move with respect to the ocular implant.

In some embodiments, the system includes a fluid and a fluid injection mechanism adapted to inject the fluid (such as, e.g., a dilatation agent adapted to dilate tissue) into Schlemm's canal of the eye through the cannula. In some such embodiments, the channel opening tool has a fluid lumen and the fluid injection mechanism is adapted to inject fluid through the channel opening tool fluid lumen. In some such embodiments, the channel opening tool may have a distal opening communicating with the fluid lumen and/or a liner tube surrounding the fluid lumen.

In some embodiments, the fluid injection mechanism has a piston disposed in a cylinder. In such embodiments in which the proximal control includes a handle, the fluid injection mechanism may also include an injection tube extending from an outlet of the cylinder to the handle.

Another aspect of the invention provides a method of treating glaucoma in a human eye including the steps of: inserting a distal exit port of a cannula at least partially into Schlemm's canal of the eye; delivering a channel tool through the cannula into Schlemm's canal; delivering an ocular implant through the cannula into Schlemm's canal; and removing the channel tool and the cannula from the eye while leaving the ocular implant in place within Schlemm's canal. In some embodiments, the method includes the step of delivering a dye through the channel tool and observing the behavior of the dye to identify the location of obstructions within Schlemm's canal.

In some embodiments, the method includes the step of opening a channel in Schlemm's canal with the channel tool. The step of opening a channel may include the step of moving the channel tool within Schlemm's canal. The step of opening a channel may include the step of delivering a fluid (such as a dilatation agent, a therapeutic agent and/or a dye) through the channel tool by, e.g., moving the fluid through an obstruction within Schlemm's canal to increase fluid communication between adjacent segments of Schlemm's canal.

In some embodiments, the delivering steps include the step of delivering the channel opening tool and the ocular implant without removing the distal tip of the cannula from the eye. Some embodiments of the method include the step of moving the channel opening tool and the ocular implant with respect to each other within Schlemm's canal.

In some embodiments, the delivering steps include the step of delivering the ocular implant over the channel opening tool. In some embodiments, the inserting step includes the step of inserting the distal exit port of the cannula at least partially into Schlemm's canal of the eye through an ab interno approach. In other embodiments, the inserting step includes the step of inserting the distal exit port of the cannula at least partially into Schlemm's canal of the eye through an ab externo approach.

Yet another aspect of the invention provides an ocular implant and delivery system including a channel tool adapted to extend through at least a portion of Schlemm's canal of a human eye and to determine whether the Schlemm's canal portion provides a suitable location for the delivery of an ocular implant; a cannula comprising a distal opening adapted to deliver the channel tool and the ocular implant into Schlemm's canal of the eye; and a proximal control adapted to move the channel tool with respect to the cannula.

Still another aspect of the invention provides a method of treating glaucoma in a human eye including the steps of inserting a distal exit port of a cannula at least partially into Schlemm's canal of the eye; delivering a channel tool through the cannula into Schlemm's canal using a proximal control; and removing the channel tool and the cannula from the eye while leaving the ocular implant in place within Schlemm's canal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a stylized representation of an exemplary medical procedure in accordance with this detailed description.

FIGS. 2A and 2C are perspective views illustrating an ocular implant and delivery system and method according to an embodiment of this invention.

FIG. 2B is an enlarged perspective view of a cannula and channel tool of the system shown in FIG. 2A.

FIGS. 18A and 18B are stylized perspective views of eyes in which ocular implants have been placed in Schlemm's canal.

FIG. 19A is a stylized perspective view of an eye in which an ocular implant has been placed with an inlet in the anterior chamber and the remainder of the device in Schlemm's canal.

FIG. 19B is a stylized perspective view of an eye in which an ocular implant has been placed so that it lies entirely within Schlemm's canal.

FIGS. 20A-D and 21 show details of a method of using the system of this invention.

FIG. 23A is a perspective view of certain components of an ocular implant and delivery system according to an embodiment of this invention.

FIG. 23B is a detail view of the distal end of the system shown in FIG. 23A.

FIG. 24 is an elevational view of a cannula, push tube ocular plant of a system according to an embodiment of this invention.

FIGS. 25A-B show details of the connection between the ocular implant and push tube shown in FIG. 24.

DETAILED DESCRIPTION OF THE INVENTION

Figure 2C:
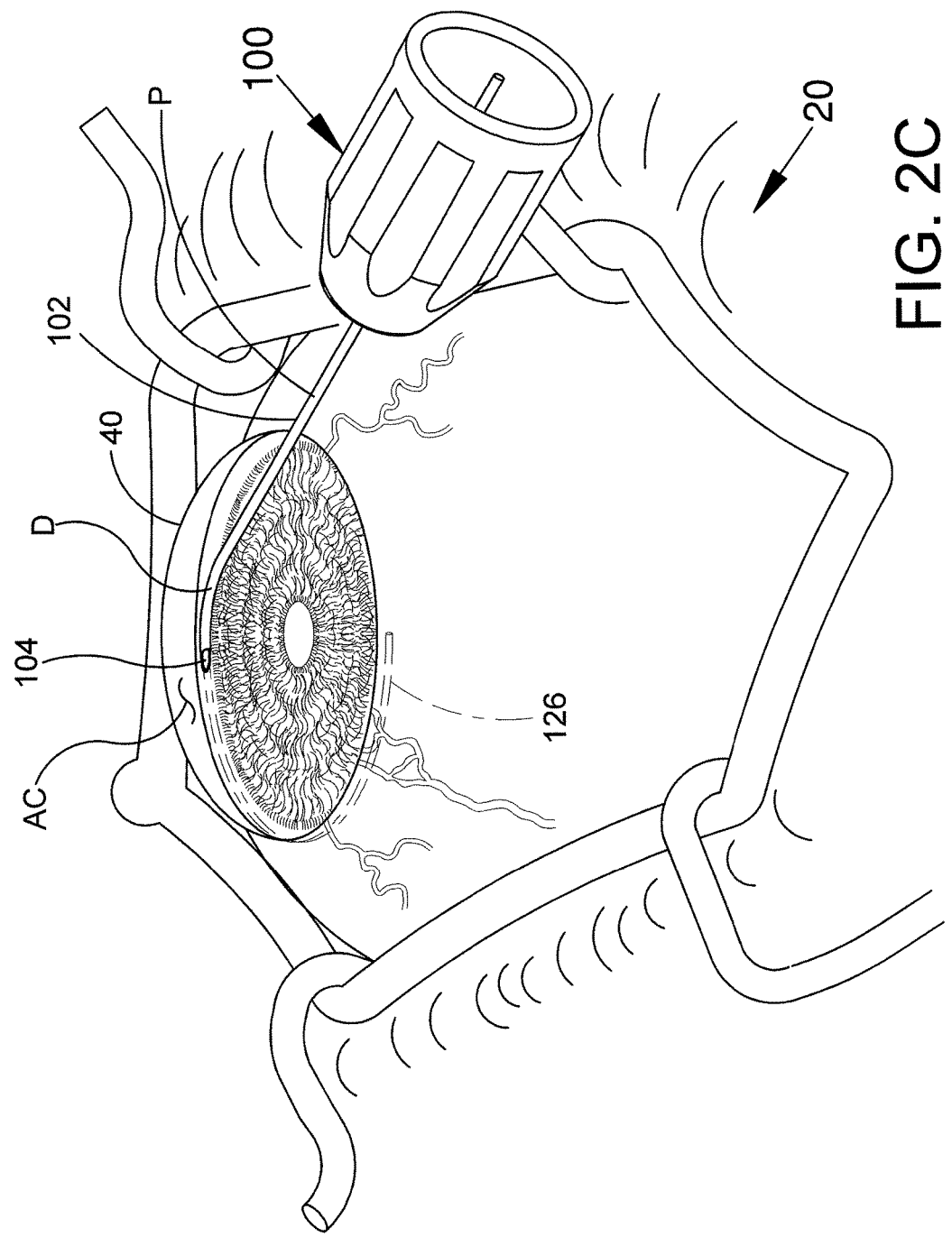

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

FIG. 1 is a stylized representation of an exemplary medical procedure in accordance with this detailed description. In this exemplary medical procedure, a physician is treating an eye 20 of a patient P using a therapy system 100, such as an ocular implant and delivery system. In the exemplary procedure of FIG. 1, the physician is holding a handle portion of therapy system 100 in his or her right hand RH. The physician's left hand (not shown) may be used to hold the handle H of a gonio lens 23. It will be appreciated that some physician's may prefer holding the therapy system handle in the left hand and the gonio lens handle H in the right hand RH.

During the exemplary procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 102 is visible in Detail A. A shadow-like line indicates the location of Schlemm's canal SC which is lying under various tissue (e.g., the trabecular meshwork) that surround the anterior chamber. A distal opening 104 of cannula 102 is positioned near Schlemm's canal SC of eye 20. In some methods in accordance with this detailed description, distal opening 104 of cannula 102 is placed in fluid communication with Schlemm's canal SC. When this is the case, a device (e.g., an implant or a delivery tool for an implant) may be advanced through distal opening 104 and into Schlemm's canal SC.

FIG. 2A is a perspective view further illustrating therapy system 100 and eye 20 shown in the previous figure. In FIG. 2A, cannula 102 of therapy system 100 is shown extending through a cornea 40 of eye 20. A distal portion of cannula 102 is disposed inside the anterior chamber defined by cornea 40 of eye 20. In the embodiment of FIG. 2A, cannula 102 is configured so that a distal opening 104 of cannula 102 can be placed in fluid communication with Schlemm's canal.

In the embodiment of FIGS. 2A and 2B, a channel tool 126 is disposed in a lumen defined by cannula 102. Therapy system 100 includes a mechanism that is capable of advancing and retracting the channel tool along the length of cannula 102. The channel tool 126 may be placed in Schlemm's canal of eye 20 by advancing the channel tool through distal opening 104 of cannula 102 while distal opening 104 is in fluid communication with Schlemm's canal.

FIG. 2B is an enlarged detail view further illustrating cannula 102 of therapy system 100. In the illustrative embodiment of FIG. 2B, channel tool 126 has been advanced through distal opening 104 of cannula 102. Cannula 102 of FIG. 2B defines a passageway 124 that fluidly communicates with distal opening 104. Channel tool 126 may be moved along passageway 124 and through distal opening 104 by therapy system 100. Therapy system 100 includes a proximal control mechanism 101 disposed outside of the eye that is capable of performing this function.

FIG. 2C is an enlarged perspective view further illustrating eye 20 shown in FIG. 2A. In FIG. 2C, a cannula 102 of a therapy system 100 can be seen extending through cornea 40 of eye 20 so that a distal portion D of cannula 102 disposed in the anterior chamber AC of eye 20. A proximal portion P of cannula 102 disposed outside anterior chamber AC in FIG. 2C. In the embodiment of FIG. 2C, cannula 102 has been positioned so that distal port 104 of cannula 102 is in fluid communication with Schlemm's canal of eye 20. A channel tool 126 of therapy system 100 has been advance through distal port 104 of cannula 102 and into Schlemm's canal of eye 20.

Figure 3:
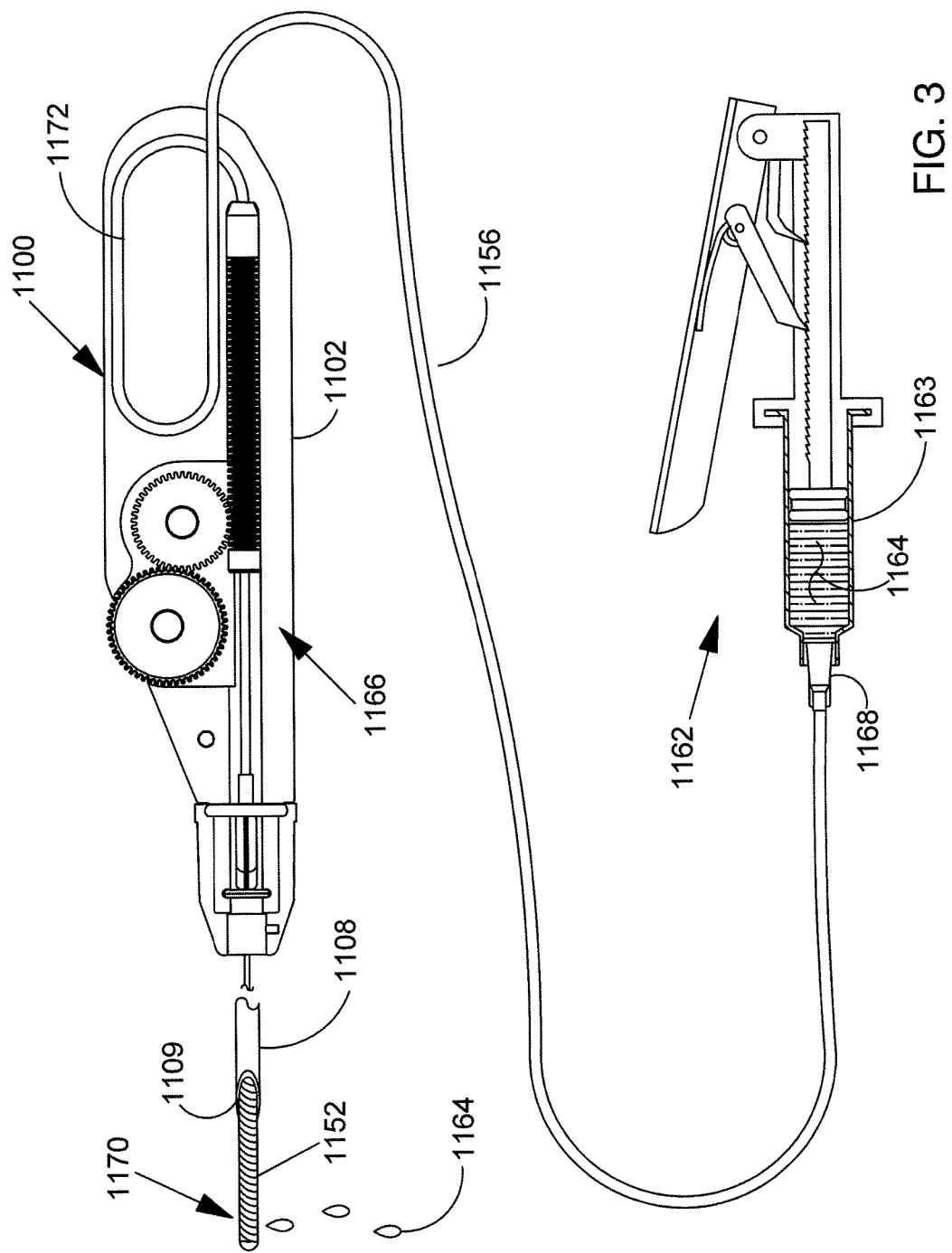
FIG. 3 is a stylized partial cross-sectional and partial plan view of an ocular implant and delivery system according to an embodiment of this invention.

FIG. 3 is a stylized plan view illustrating an exemplary therapy system 1100 in accordance with this detailed description. The therapy system 1100 of FIG. 3 includes a channel tool 1152, a cannula 1108, and a fluid injection assembly 1162. In the embodiment of FIG. 3, fluid injection assembly 1162 includes a syringe (i.e., a piston disposed in a cylinder) 1163 that is filled with fluid 1164. Therapy system 1100 of FIG. 3 may be used, for example, to determine whether Schlemm's canal of an eye provides a suitable location for the delivery of an ocular implant and/or to open Schlemm's canal of the eye.

Exemplary methods in accordance with this detailed description may include the step of advancing a distal portion of channel tool 1152 through the distal port 1109 of cannula 1108 into Schlemm's canal of an eye. If resistance is encountered as channel tool 1152 is advanced, the user is provided with an indication that Schlemm's canal is partially or completely blocked. The channel tool 1152 may be advanced through the blockage to open a channel in Schlemm's canal and/or to increase fluid communication between adjacent segments of Schlemm's canal. Alternatively or additionally, the channel tool may also used to inject fluid 1164 into Schlemm's canal to open the canal and/or to provide lubrication for further advancement of the channel tool into the canal. In addition to locating obstructions using tactile feel, a physician may use channel tool 1152 to visually identify obstructions. For example, channel tool 1152 may be used to inject a visualization enhancing fluid (e.g., a dye) into Schlemm's canal. As fluid is injected into Schlemm's canal, the physician may observe the movement of that fluid within Schlemm's canal using a microscope and a gonio lens as shown in FIG. 1. Therapy system 1100 may also be used to deliver an implant, such as an aqueous humor drainage device, into Schlemm's canal of the eye. When this is the case, the aqueous humor drainage device may be mounted on channel tool 1152.

In FIG. 3, channel tool 1152 is shown extending through a distal port 1109 of cannula 1108. Cannula 1108 is coupled to a proximal control 1102 of therapy system 1100. Proximal control 1102 includes a mechanism 1166 that is capable of advancing and retracting channel tool 1152. In the exemplary embodiment of FIG. 3, mechanism 1166 is substantially disposed inside proximal control 1102.

In the embodiment of FIG. 3, channel tool 1152 includes a coiled cable. An injection tube 1156 extends from a fluid injection port 1168 in syringe 1163 through proximal control 1102 to deliver fluid 1164 to channel tool 1152. Fluid 1164 that has exited channel tool 1152 is represented by a number of fluid drops in the stylized plan view of FIG. 3. Fluid injection assembly 1162 includes a mechanism including a lever. The mechanism cooperates with syringe 1163 to dispense fluid (e.g., the drops shown in FIG. 3). In the exemplary embodiment of FIG. 3, fluid injection assembly 1162 will dispense a controlled volume of fluid each time the lever is actuated. In some exemplary methods, fluid is injected into Schlemm's canal as a series of controlled-volume increments to gently separate the walls of the canal in areas where Schlemm's canal is obstructed. It will be appreciated that other embodiments of the fluid injection assembly 1162 are possible without deviating from the spirit and scope of the present detailed description. For example, fluid injection assembly 1162 may employ a screw type ratcheting plunger which can dispense a controlled volume per click of the ratchet mechanism.

It will be appreciated that fluid 1164 may comprise various materials without deviating from the spirit and scope of the present detailed description. Examples of fluids that may be suitable in some applications include water, saline, hyaluronic acid and/or viscoelastic. The term "viscoelastic" is sometimes used to describe various viscoelastic materials that are injected into the eye as part of a surgical procedure. Viscoelastics for use in ophthalmic surgery are commercially available from Bausch and Lomb Incorporated (Rochester, N.Y., U.S.A.) and Alcon, Incorporated (Hunenberg, Switzerland). Viscoelastics may comprise, for example, hyaluronic acid. Hyaluronic acid is a material that is naturally found in the vitreous humor that fills the posterior chamber of the eye. Accordingly, this material is well suited for use in ophthalmic surgery. Hyaluronic acid is also known as hyaluronan and hyaluronate.

With reference to FIG. 3, a loop 1172 is formed in injection tube 1156. In some useful embodiments, loop 1172 is sized to provide a level of travel necessary to advance the distal end channel tool 1152 through the entire length of Schlemm's canal. In the exemplary embodiment of FIG. 3, loop 1172 is disposed inside proximal control 1102.

Figure 4A:
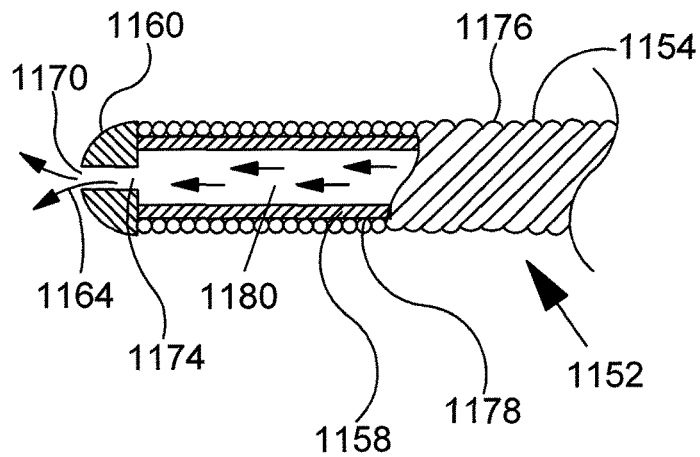
FIG. 4A is a partial cross-sectional view of a distal portion of a channel tool according to an embodiment of this invention.

FIG. 4A is a partial cross-sectional view showing a distal portion of an exemplary channel tool 1152 in accordance with this detailed description. In this embodiment, channel tool 1152 includes a cable 1154 and a distal tip 1160 at the distal end of cable 1154. Distal tip 1160 may be attached to cable 1154, for example, by welding. Distal tip 1160 is rounded so as to be atraumatic. Distal tip 1160 has a tip lumen 1174 fluidly communicating with a distal opening 1170. In this embodiment, cable 1154 is formed as a helical coil (formed, e.g., from stainless steel, nitinol or other suitable material) having a plurality of filars 1176 forming a hollow tube-like structure. In some particularly useful embodiments, cable 1154 comprises a torque cable. Torque cables that may be suitable in some applications are commercially available from Fort Wayne Metals, Inc. (Fort Wayne, Ind., U.S.A) and Asahi Intecc Co. Ltd. (Nagoya, Aichi Prefecture, Japan). In the embodiment of FIG. 4A, each filar 1176 has a generally helical shape. In the embodiment of FIG. 4A, filars 1176 of cable 1154 define a cable lumen 1178. Lubricity of the coil can be enhanced by the application of a surface coating (PTFE, heparin, etc.) which will further reduce potential trauma and facilitate smooth predictable advancement. A liner tube 1158 is disposed inside cable lumen 1178. Liner tube 1158 may be formed, e.g., from polyimide and defines a liner lumen 1180 that fluidly communicates with tip lumen 1174 defined by distal tip 1160. FIG. 4A includes a plurality of arrows representing fluid 1164 flowing through tip lumen 1174 of channel tool 1152 and shown exiting distal opening 1170. Fluid (such as, e.g., viscoelastic) injected through this opening may be used, for example, to gently separate the walls of Schlemm's canal in areas where the canal walls have collapsed and or adhered to each other. The newly created space will provide a passageway for the cable to atraumatically advance without causing tearing or puncturing into the canal.

Figure 4B:
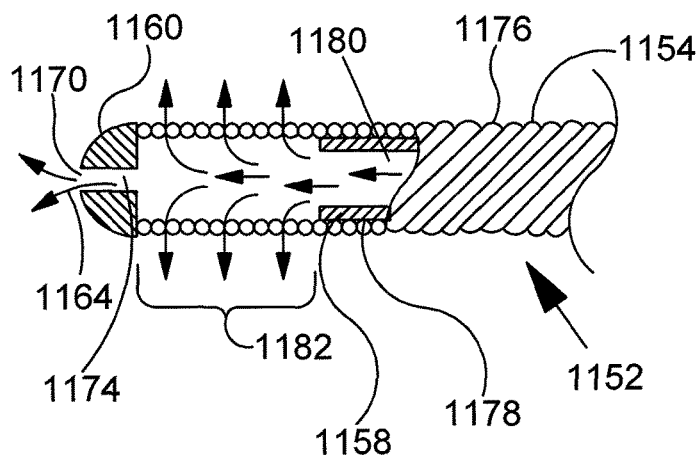
FIG. 4B is a partial cross-sectional view of a distal portion of a channel tool according to another embodiment of this invention.

In the view of FIG. 4A, liner tube 1158 is positioned so that its distal end extends through cable 1154 to a proximal surface of distal tip 1160. In the view of FIG. 4B, liner tube 1158 ends proximally of the proximal surface of distal tip 1160 to expose a distal portion 1182 of cable 1154 to fluid (such as, e.g., viscoelastic) within lumen 1180. This fluid can then flow between adjacent filars 1176 of cable 1154, as shown by arrows 1164. Fluid injected between adjacent filars 1176 may be used, for example, to gently separate the walls of Schlemm's canal in areas where the canal walls have collapsed upon each other.

Figure 5:
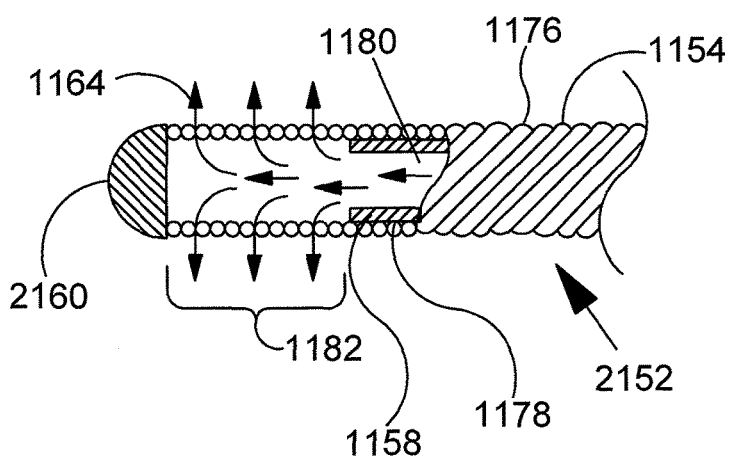
FIG. 5 is a partial cross-sectional view of a distal portion of a channel tool according to yet another embodiment of this invention.

FIG. 5 is a partial cross-sectional view showing a distal portion of a channel tool 2152 according to another embodiment of this invention. In this embodiment, distal tip 2160 is closed, i.e., it lacks the distal opening shown in the embodiment of FIGS. 4A and 4B. Other elements of this embodiment are the same as those of the FIGS. 4A and 4B embodiment and therefore have the same element numbers. As shown in FIG. 5, a distal portion 1182 of cable 1154 is exposed to fluid within lumen 1180. When this is the case, fluid (such as, e.g., viscoelastic) can flow between adjacent filars 1176 of cable 1154. Fluid injected between adjacent filars 1176 may be used, for example, to gently dilate the walls of Schlemm's canal to a larger dimension than the channel tool itself. An enlarged lumen is useful in accommodating an even larger device, such as an implant.

The channel tools of this invention (such as channel tools 1152 and 2152 described above) may be used to determine whether a portion of Schlemm's canal provides a suitable location for the delivery of an ocular implant. The channel tools may also be used to open a blocked or partially blocked portion of Schlemm's canal by injecting fluid (such as viscoelastic) and/or by mechanical force as the channel tool is advanced through Schlemm's canal. The channel tool may be used to deliver a canal dilation agent such as trypan blue or Indocyannine green (ICG), a colored agent or dye to provide enhanced viewing of the canal by a clinician and/or a therapeutic agent (such as, e.g., therapeutic agents enhancing the collector channels/trabecular meshwork, including ethacrynic acid, cytochalasin, rho kinase inhibitors). In some cases, enhanced viewing of Schlemm's canal may be achieved using a fluorescent dye in conjunction with black light.

Figure 6:
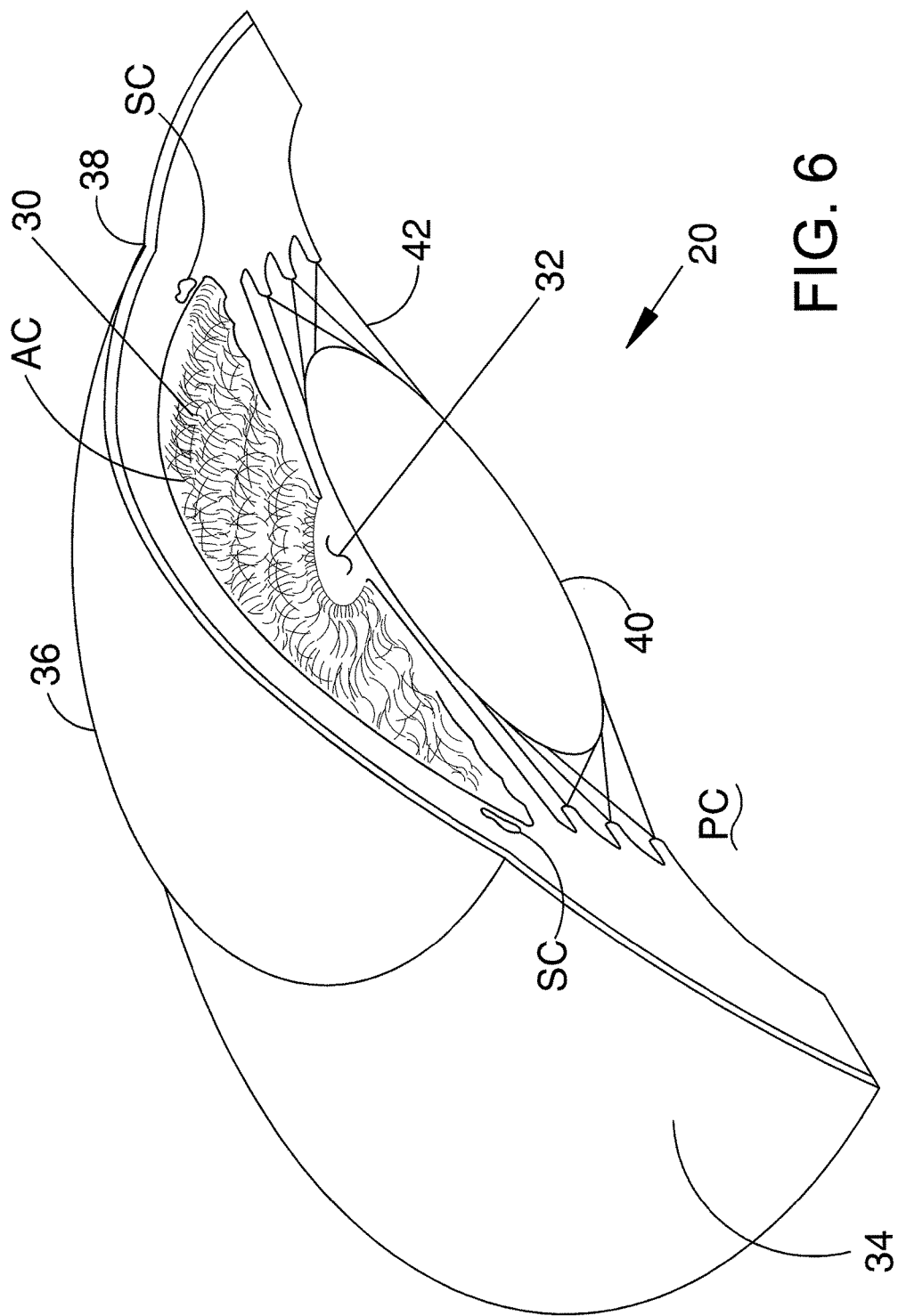
FIG. 6 is a stylized perspective view illustrating the anatomy of an eye.
Figure 7:
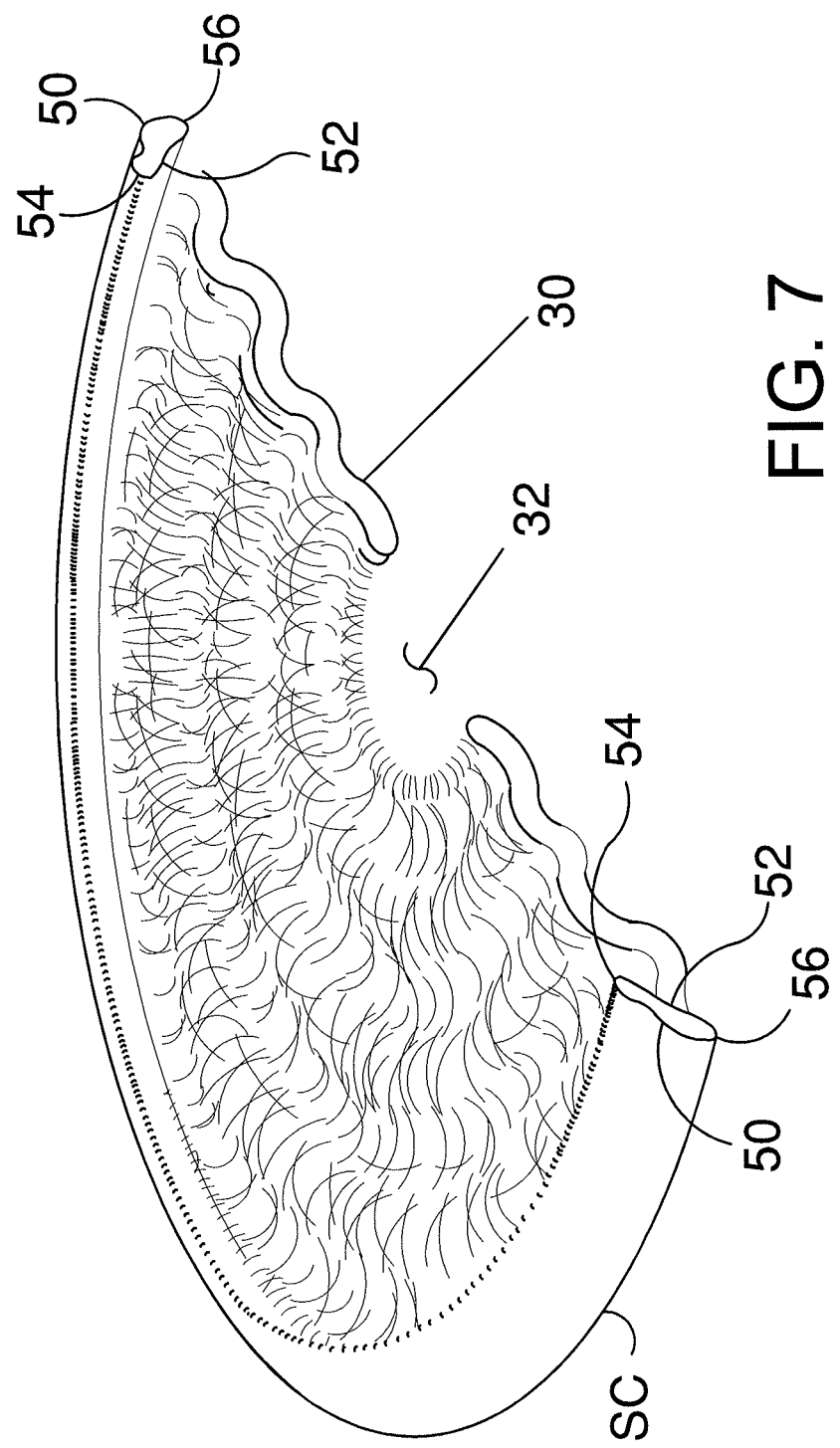
FIG. 7 is a stylized perspective view showing Schlemm's canal and an iris of the eye shown in the previous figure.
Figure 8:
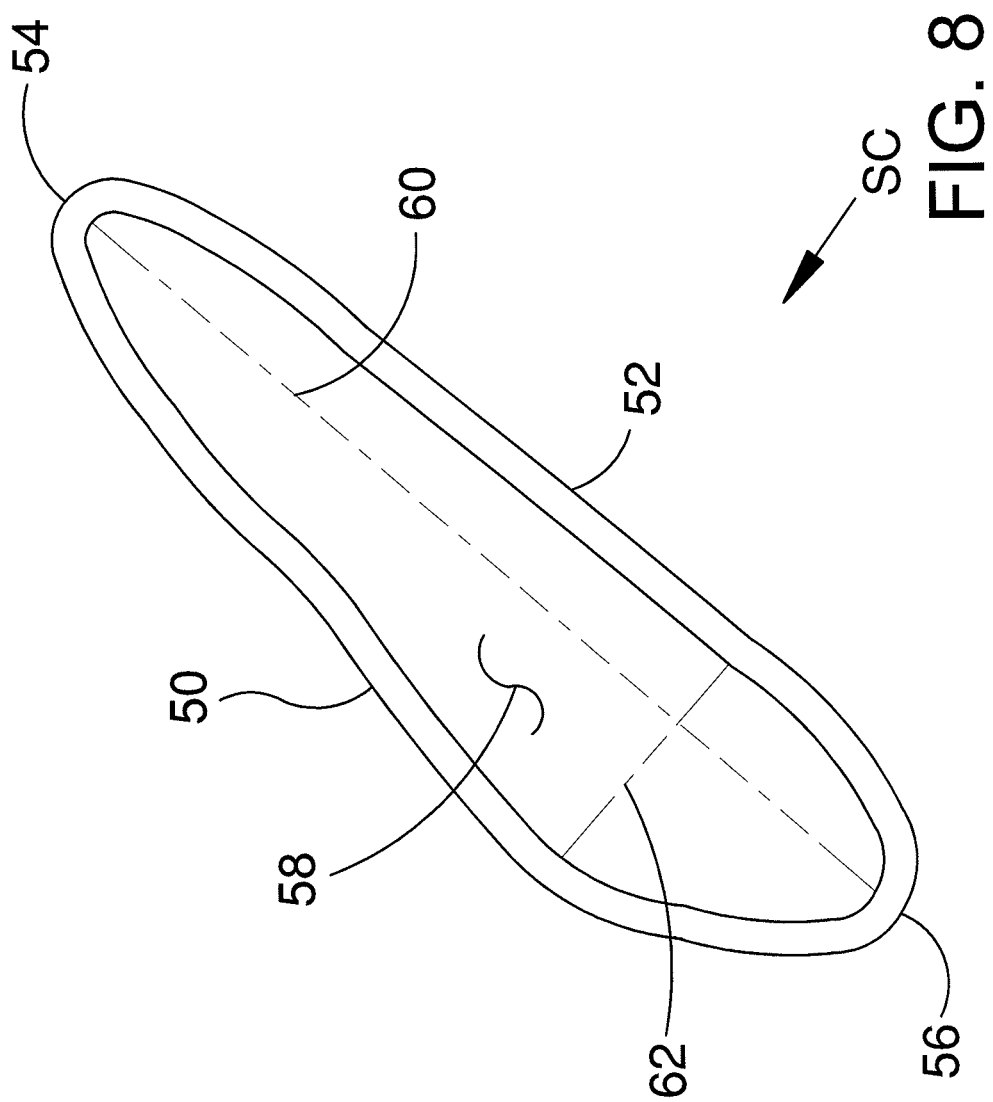
FIG. 8 is an enlarged cross-sectional view further illustrating Schlemm's canal shown in the previous figure.

The system of this invention may be used to deploy a channel tool and/or an ocular implant via an ab interno approach or an ab externo approach. FIGS. 6-8 show details of a human eye. FIG. 6 is an enlarged perspective view illustrating a portion of eye 20 shown as a cross-sectional view created by a cutting plane passing through the center of pupil 32. Eye 20 includes an iris 30 defining a pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid know as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 6. In a healthy eye, aqueous humor flows out of anterior chamber AC and into Schlemm's canal SC. Aqueous humor exits Schlemm's canal SC and flows into a number of collector channels (shown as CC in FIG. 9). After leaving Schlemm's canal SC, aqueous humor is absorbed into the venous blood stream and carried out of the eye.

FIG. 7 is a stylized perspective view showing Schlemm's canal SC and iris 30 of eye 20 shown in the previous figure. In FIG. 7, Schlemm's canal SC is shown encircling iris 30. With reference to FIG. 7, it will be appreciated that Schlemm's canal SC may overhang iris 30 slightly. Iris 30 defines a pupil 32. In the exemplary embodiment of FIG. 7, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 7, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. First major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 7, it will be appreciated that first major side 50 is further from pupil 32 than second major side 52. The high pressures inside the eye of a patient suffering from glaucoma, may cause the inner major wall of Schlemm's canal to be pressed against the outer major wall of the canal. Over time, adhesions may form between the inner major wall and the outer major wall. These adhesions obstruct Schlemm's canal, inhibit circumferential flow and divide the canal into isolated compartments. Exemplary methods in accordance with this detailed description may be used by a physician to examine Schlemm's canal and identify to location and nature of such obstructions. For example, a channel tool in accordance with this detailed description may be used to inject a fluid (e.g., dye) into Schlemm's canal. As fluid is injected into Schlemm's canal, the physician may observe the movement of that fluid within Schlemm's canal using a microscope and a gonio lens as shown in FIG. 1. Studying Schlemm's canal in this fashion allows the physician to achieve a clear understanding of the anatomical structure of the eye being studied. This knowledge will inform the physician's decision making when determining when and where to place aqueous humor drainage devices.

FIG. 8 is an enlarged cross-sectional view further illustrating Schlemm's canal SC shown in the previous figure. As shown in FIG. 8, Schlemm's canal SC has a wall W defining a lumen 58. The shape of Schlemm's canal SC is somewhat irregular, and it can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 8.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 8, it will be appreciated that Schlemm's canal SC comprises a first major side 50, a second major side 52, a first minor side 54, and a second minor side 56. In the exemplary embodiment of FIG. 8, first major side 50 is longer than both first minor side 54 and second minor side 56. Also in the exemplary embodiment of FIG. 8, second major side 52 is longer than both first minor side 54 and second minor side 56.

Figure 9:
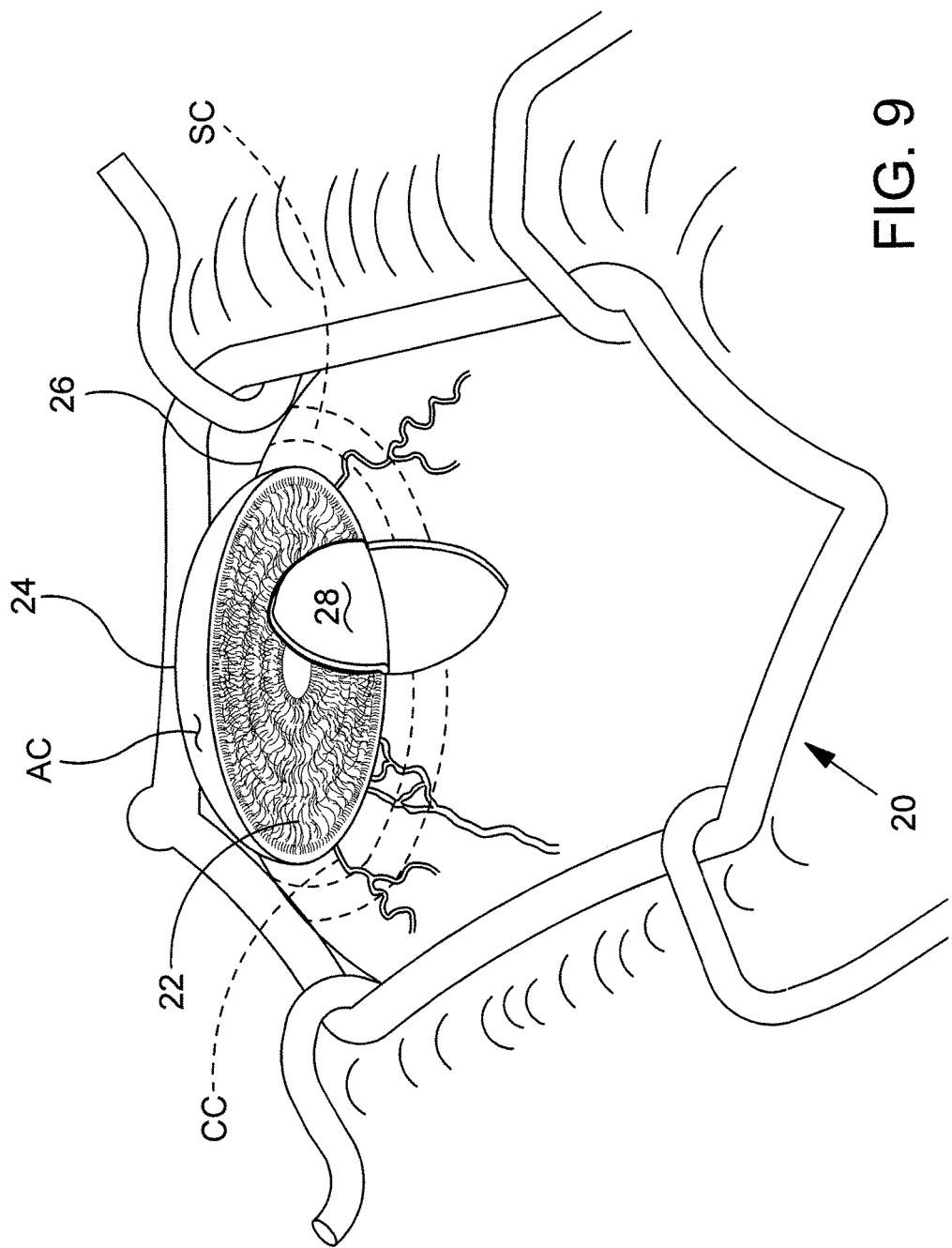
FIG. 9 is a stylized perspective view of an eye in which a scleral flap has been formed.

FIG. 9 is a stylized perspective view showing an eye 20. In the embodiment of FIG. 9, the upper and lower eyelids of the eye are held open with surgical tools so that the eye is accessible to a physician. Cornea 24 of eye 20 meets the sclera 26 of eye 20 at the limbus. The Schlemm's canal SC of eye 20 is disposed below sclera 26. Schlemm's canal SC is illustrated with dashed lines in FIG. 9. These dashed lines generally encircle the iris 22 of eye 20.

Glaucoma may be treated, for example, by implanting one or more aqueous humor drainage devices in the eye. The several figures that follow illustrate exemplary methods of an ab externo approach for using a channel tool to determine whether the Schlemm's canal portion provides a suitable location for the delivery of an ocular implant and for placing an aqueous humor drainage device into an eye. Two incisions have been made in sclera 26 of eye 20 of FIG. 9. These two incisions define a first scleral flap 28. The two incisions defining first scleral flap 28 extend through less than the entire thickness of sclera 26. Accordingly, these two incisions may be referred to as partial thickness incisions. As shown in FIG. 9, first scleral flap 28 has been folded upward.

Figure 10:
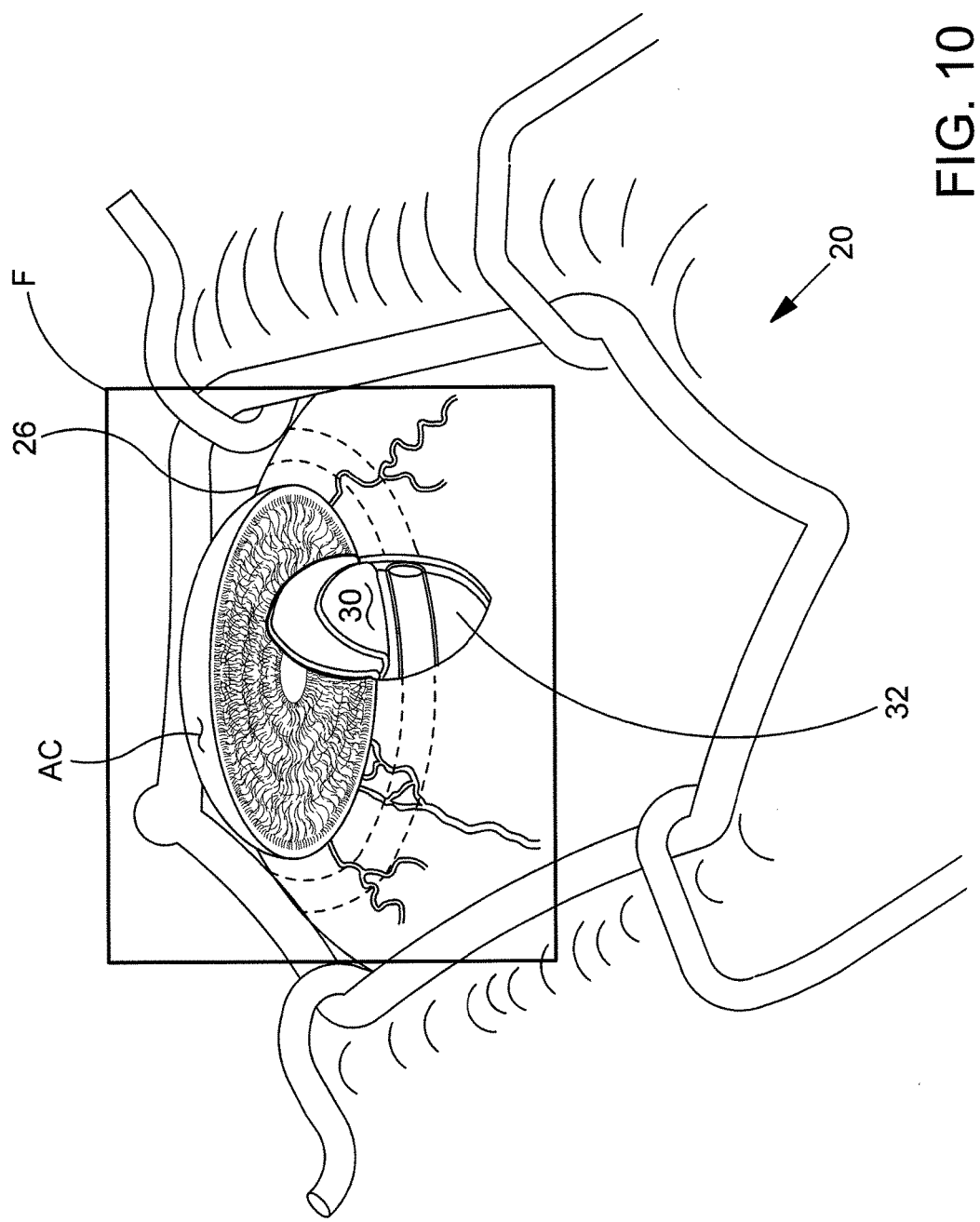
FIG. 10 is a stylized perspective view of the eye of FIG. 9 in which a second scleral flap has been formed.

FIG. 10 is an additional perspective view of eye 20 shown in the previous figure. Two additional incisions have been made in the eye 20 of FIG. 10. These two additional incisions extend deeper into sclera 26 and define a second scleral flap 30. The incisions made in sclera 26 have formed a recess 32 in eye 20. In FIG. 10, second scleral flap 30 has been folded upward. In some useful embodiments, second scleral flap 30 is surgically removed from eye 20. When this is the case, the area formerly occupied by second scleral flap 30 may act as a reservoir for aqueous humor leaving anterior chamber AC. This reservoir may facilitate the flow of aqueous humor out of eye 20. For purposes of illustration, a portion of eye 20 is surrounded by a frame F in FIG. 10. This portion of eye 20 will be enlarged for purposes of illustration in subsequent figures.

Figure 11:
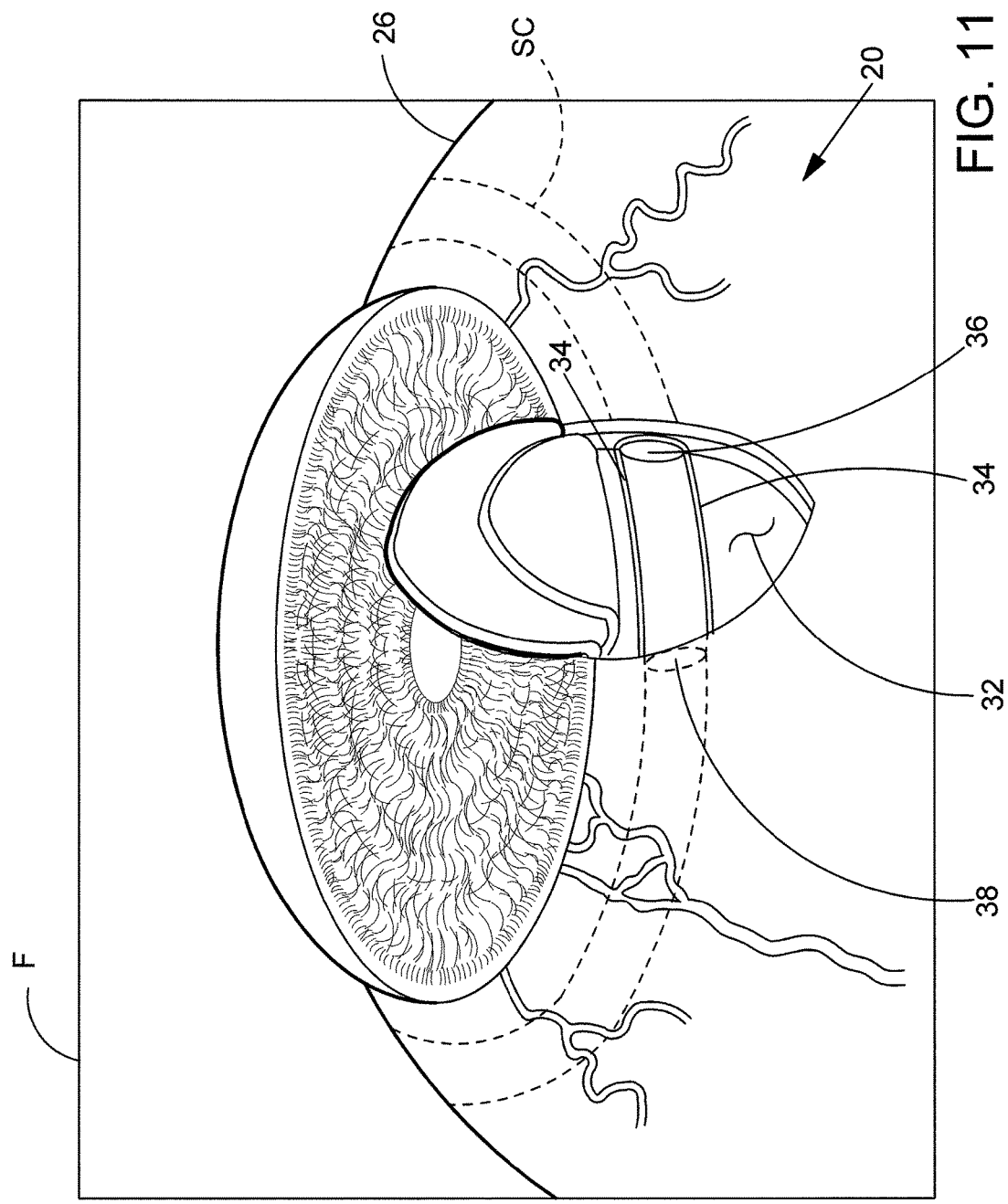
FIG. 11 is a stylized perspective view of the eye of FIGS. 9 and 10 in which openings have been made in Schlemm's canal.

FIG. 11 is an enlarged figure showing the portion of eye 20 surrounded by frame F. Incisions made in sclera 26 have formed a recess 32 in eye 20. The incisions have cut through a wall 34 of Schlemm's canal SC and extend approximately halfway through Schlemm's canal SC. The wall 34 of Schlemm's canal SC defines a first opening 36 and a second opening 38. Some exemplary methods in accordance with this detailed description may include the steps of advancing a first aqueous humor drainage device through first opening 36 and advancing a second aqueous humor drainage device through second opening 38. In some cases, a single aqueous humor drainage device may be inserted into Schlemm's canal.

Figure 12:
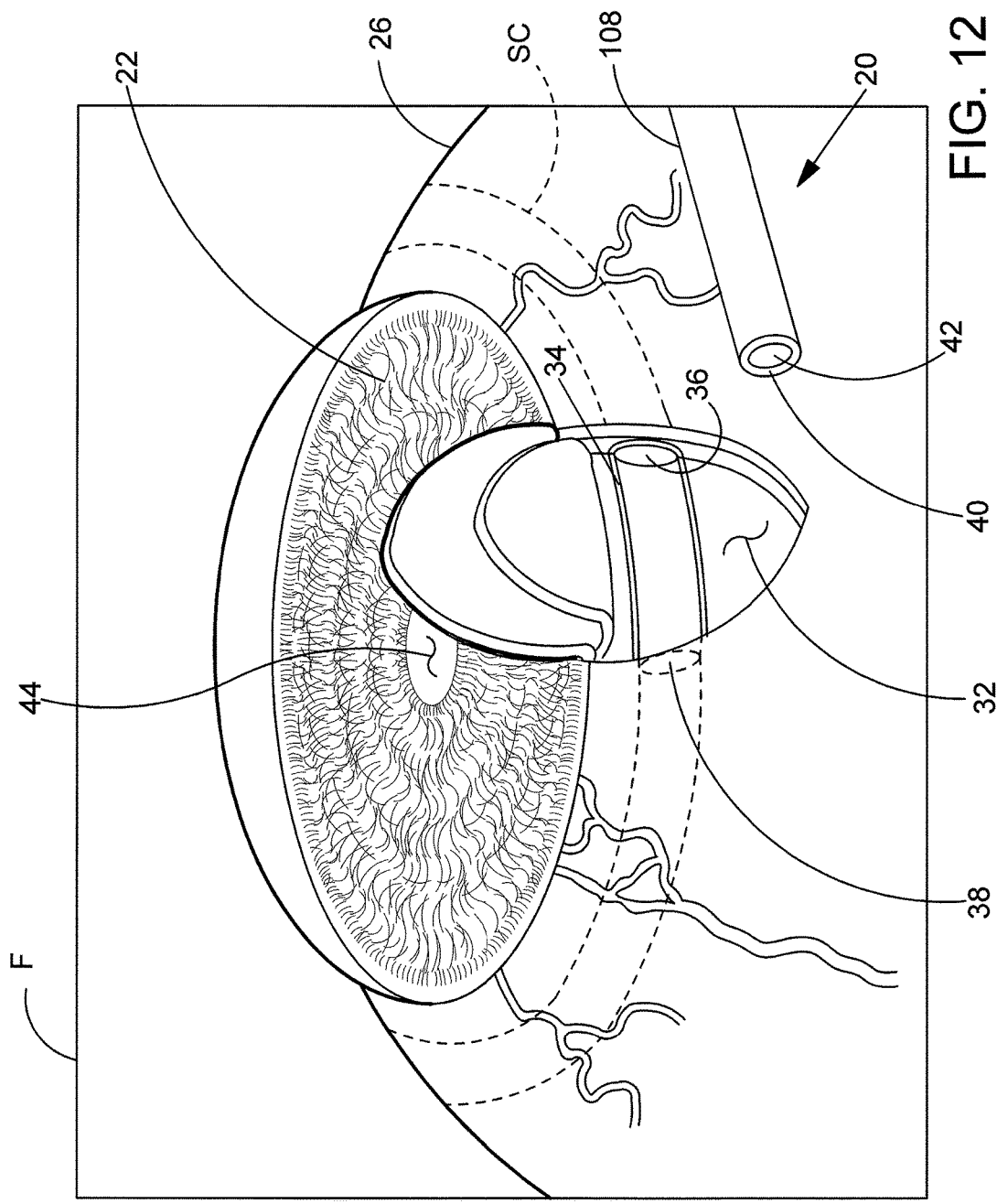
FIG. 12 is a stylized perspective view of the eye of FIGS. 9-11 showing a cannula proximate the eye.

FIG. 12 is an additional enlarged figure showing the portion of eye 20 surrounded by frame F. Schlemm's canal SC is a somewhat placid channel encircling iris 22. Iris 22 defines a pupil 44. In some cases, the Schlemm's canal of a patient suffering from glaucoma has lost some or all of its natural functionality. Due to the abnormal pressures caused by glaucoma, Schlemm's canal and related tissues may have lost the ability to respond (move) to pressure gradients. In some patients, these conditions may result in the collapse and subsequent closure of Schlemm's canal. When this is the case, the wall of Schlemm's canal may be pushed closed and may not be allowed to rebound to an open shape. Over time, the collapsed wall of Schlemm's canal may adhere to itself causing the canal to become compartmentalized. A cannula 108 has been positioned proximate recess 32. In the embodiment of FIG. 12, a distal tip portion 40 of cannula 108 has a blunt shape. Embodiments are also possible in which distal tip portion 40 of cannula 108 is configured to be inserted partially or completely into an opening cut through the wall of Schlemm's canal. In the embodiment of FIG. 12, wall 34 of Schlemm's canal SC defines a first opening 36 and a second opening 38.

Figure 13:
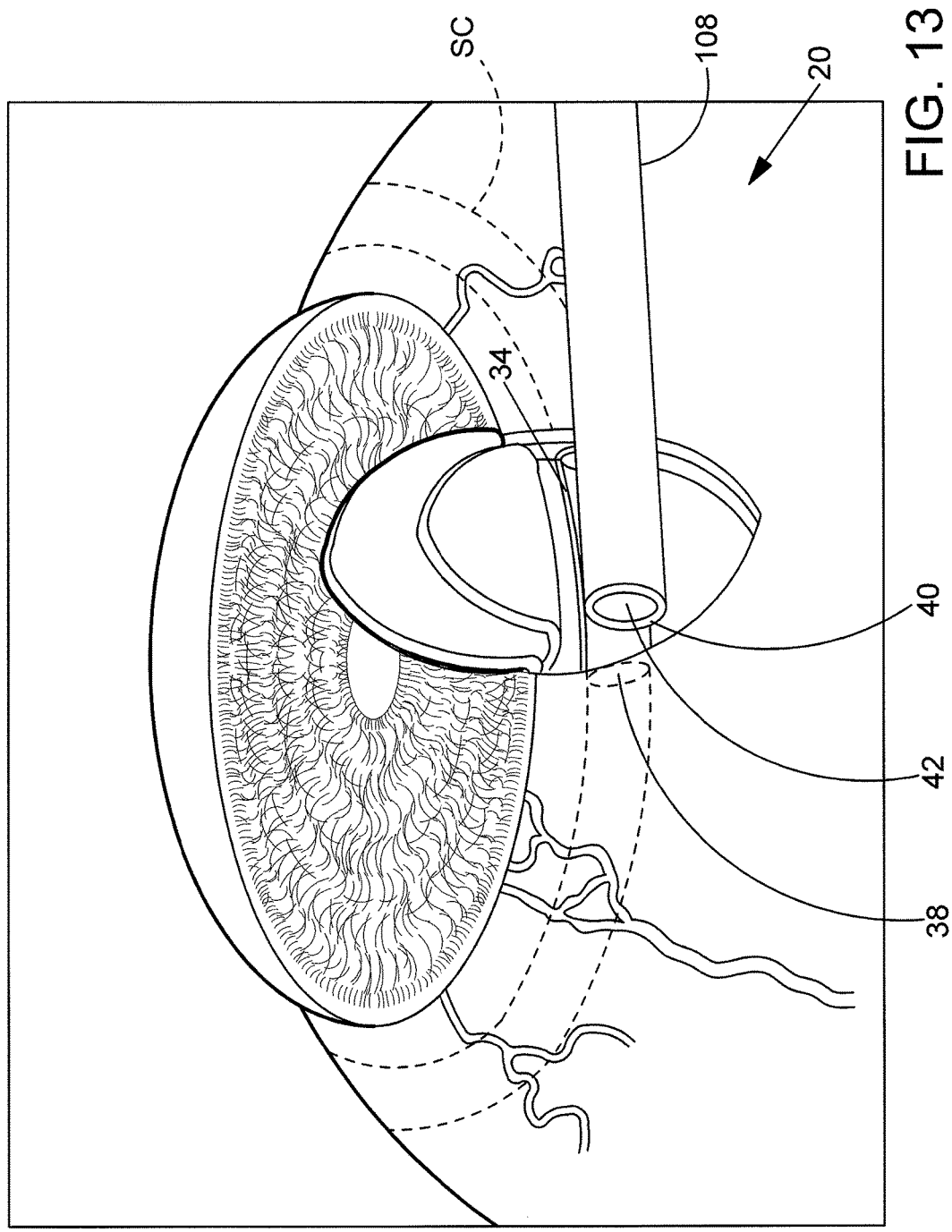
FIG. 13 is a stylized perspective view of the eye of FIGS. 9-12 showing the insertion of a distal tip of a cannula into Schlemm's canal.

FIG. 13 is an additional perspective view showing a portion of eye 20. In the embodiment of FIG. 13, distal tip portion 40 of cannula 108 has been positioned near an opening 38 cut through the wall 34 of Schlemm's canal SC. With reference to FIG. 13, it will be appreciated that distal port 42 of cannula 108 is generally aligned with opening 38 defined by wall 34 of Schlemm's canal SC. Some methods in accordance with this detailed description may include the step of aligning the distal port of a cannula with an opening cut through the wall of Schlemm's canal. A channel tool may be advanced through the distal port of the cannula and through the opening defined by the wall of Schlemm's canal. The channel tool may be used, for example, to determine whether a portion of Schlemm's canal near the opening provides a suitable location for the delivery of an aqueous humor drainage device. In some cases, the aqueous humor drainage device may be advanced through the distal port of the cannula and through the opening defined by the wall of Schlemm's canal.

Figure 14:
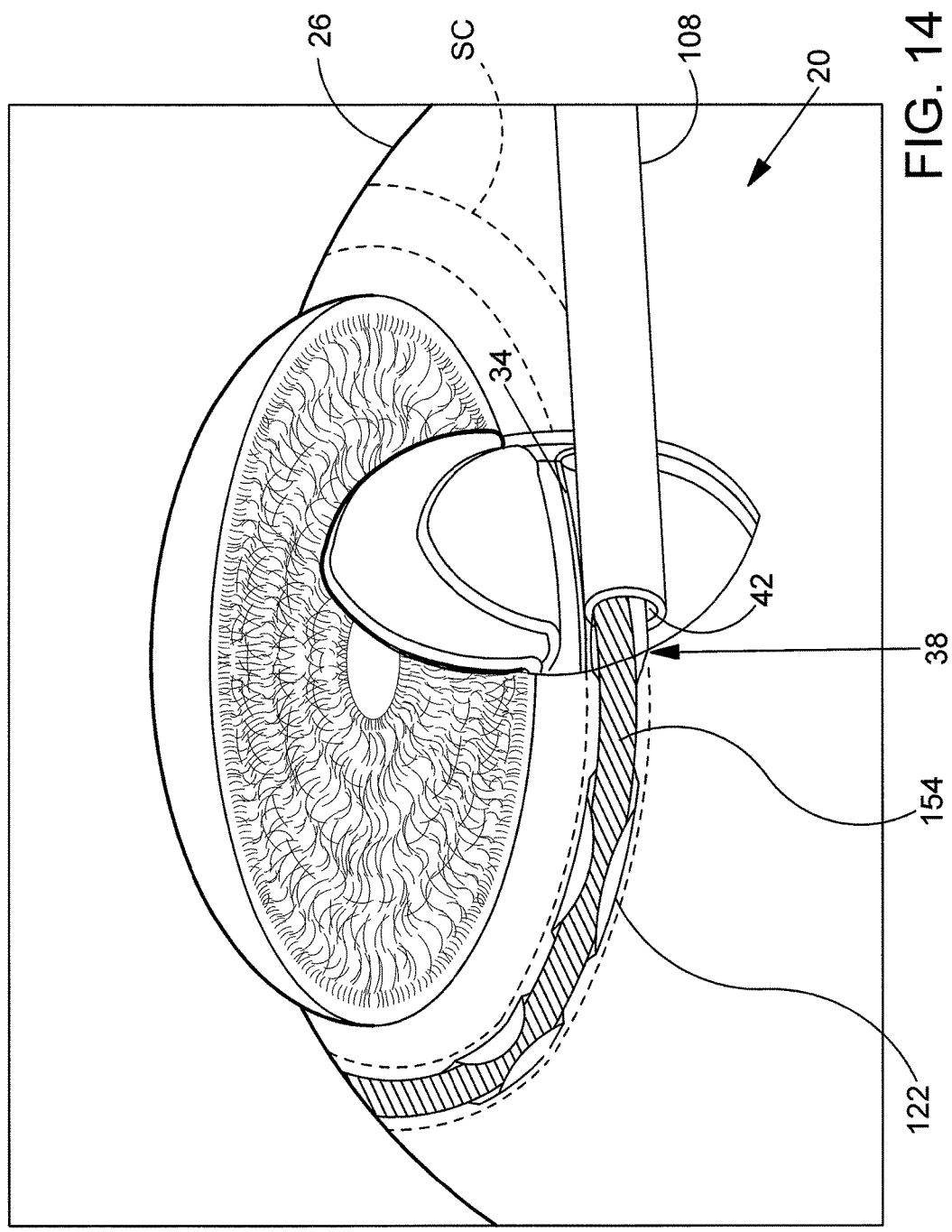
FIG. 14 is a stylized perspective view of the eye of FIGS. 9-13 showing a channel tool and ocular implant being advanced out of the cannula and into Schlemm's canal.

FIG. 14 is an additional perspective view showing a portion of eye 20. In the embodiment of FIG. 14, a channel tool 154 and an aqueous humor drainage device 122 have been advanced into Schlemm's canal SC. As shown in FIG. 14, channel tool 154 extends through distal port 42 of cannula 108 and through an opening 38 defined by wall 34 of Schlemm's canal SC. Channel tool 154 may be as described with respect to one of the embodiments described above. Therapy system 100 may include a mechanism that is capable of advancing and retracting the channel tool 154. In this embodiment, aqueous humor drainage device 122 is disposed about a distal portion of channel tool 154. Aqueous humor drainage device 122 and channel tool 154 slidingly engage each other in the embodiment of FIG. 14. Therapy system 100 may include a mechanism that is capable of advancing and retracting the aqueous humor drainage device 122.

The channel tool may be used to determine whether a Schlemm's canal portion provides a suitable location for the delivery of an ocular implant, such as aqueous humor drainage device 122. Channel tool 154 is formed with sufficient column strength to enable the tool to be advanced through an open canal without kinking. A sensation of kinking or resistance as the channel tool is advanced into Schlemm's canal will provide a user of an indication that a portion of Schlemm's canal may be partially or completely blocked and therefore unsuitable for the delivery of an ocular implant.

As described above, in some useful embodiments the channel tool 154 of therapy system 100 may have one or more distal openings that fluidly communicate with a fluid source for the injection of fluids (e.g., viscoelastic compositions) into Schlemm's canal during ophthalmic surgery. In ophthalmic surgical procedures requiring the placement of an aqueous humor drainage device in Schlemm's canal, a viscoelastic gel-like composition can be used and introduced directly into the canal to protect sensitive tissues from trauma and to provide fluid pressure for expanding collapsed portions of the canal through controlled dilatation. Viscoelastic also provides a lubricious interface between the implant and the canal to facilitate placement. When a channel tool is moved into Schlemm's canal to establish fluid flow between pockets or compartments along the canal (with or without an aqueous humor drainage device disposed about the torque cable), the injection of viscoelastic may aid in opening the canal and may provide a lubricious interface between the channel tool and the canal wall.

Figure 15:
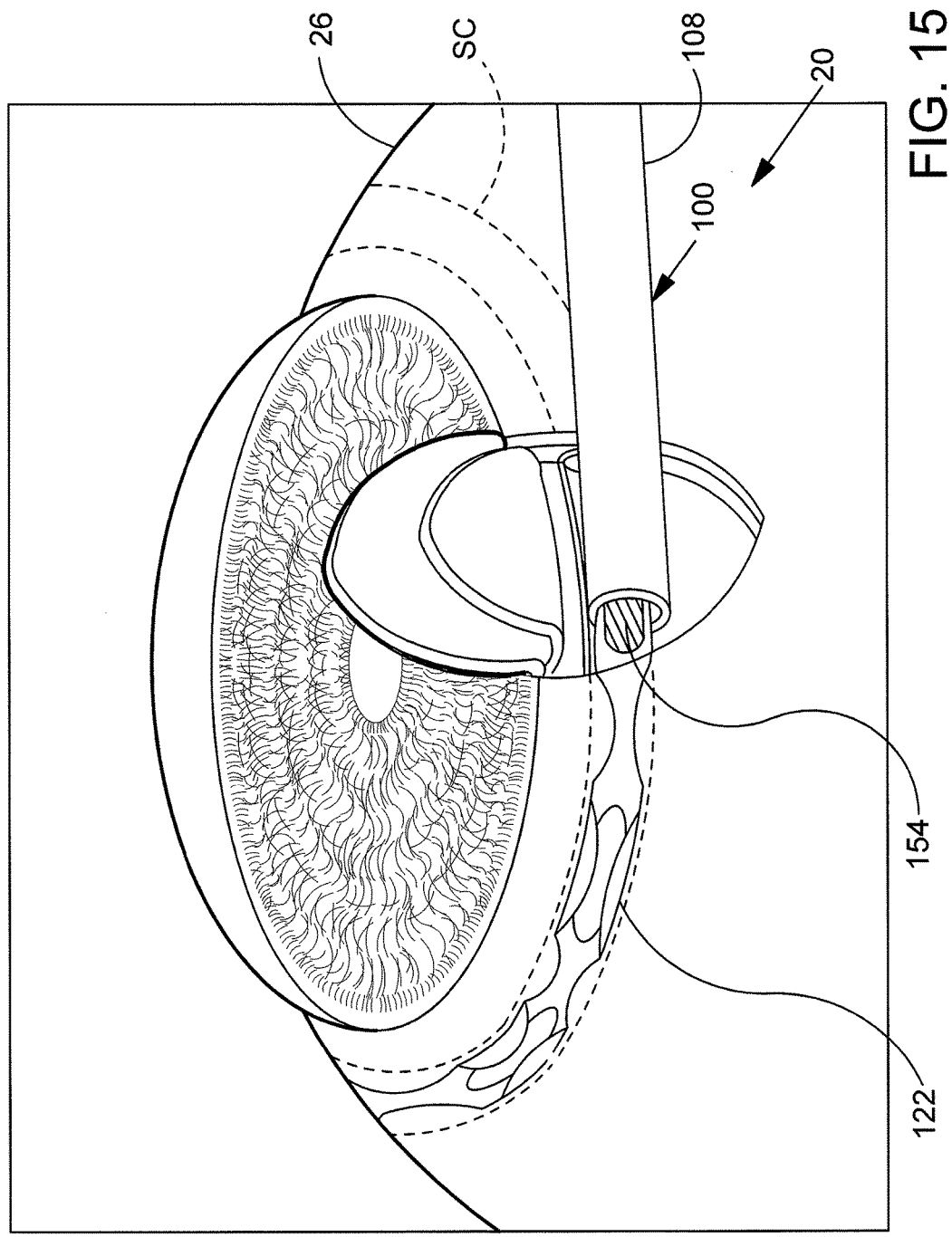
FIG. 15 is a stylized perspective view of the eye of FIGS. 9-14 showing retraction of the channel tool from Schlemm's canal, leaving the ocular implant in Schlemm's canal.

FIG. 15 is an additional perspective view showing a portion of eye 20. In the embodiment of FIG. 15, channel tool 154 has been retracted from Schlemm's canal SC leaving ocular implant 122 in place. In some useful embodiments, therapy system 100 includes a mechanism that is capable of advancing and retracting of both channel tube 154 and a push tube (not shown). When this is the case, channel tool 154 may be retracted from Schlemm's canal while the push tube prevents aqueous humor drainage device 122 from being pulled proximally.

Figure 16:
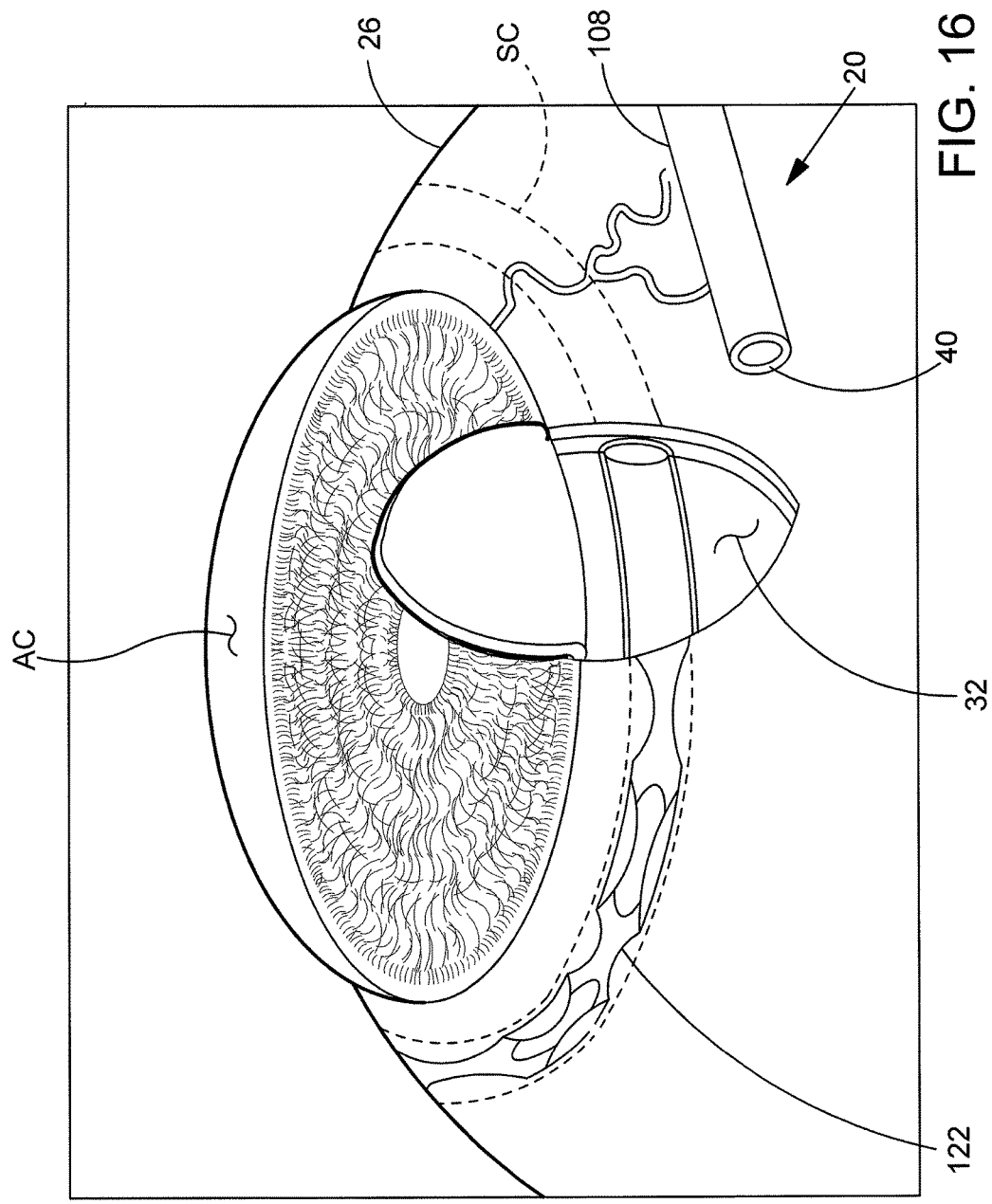
FIG. 16 is a stylized perspective view of the eye of FIGS. 9-15 showing removal of the cannula from the eye.

FIG. 16 is an additional perspective view showing a portion of eye 20. In the embodiment of FIG. 16, cannula tip 40 of cannula 108 has been moved away from Schlemm's canal SC. Aqueous humor drainage device 122 is shown residing in Schlemm's canal. As shown, the second scleral flap has been optionally surgically removed from eye 20. The portion of recess 32 formerly occupied by second scleral flap 30 may act as a reservoir for aqueous humor leaving anterior chamber AC. This reservoir may facilitate the flow of aqueous humor out of anterior chamber AC.

Figure 17:
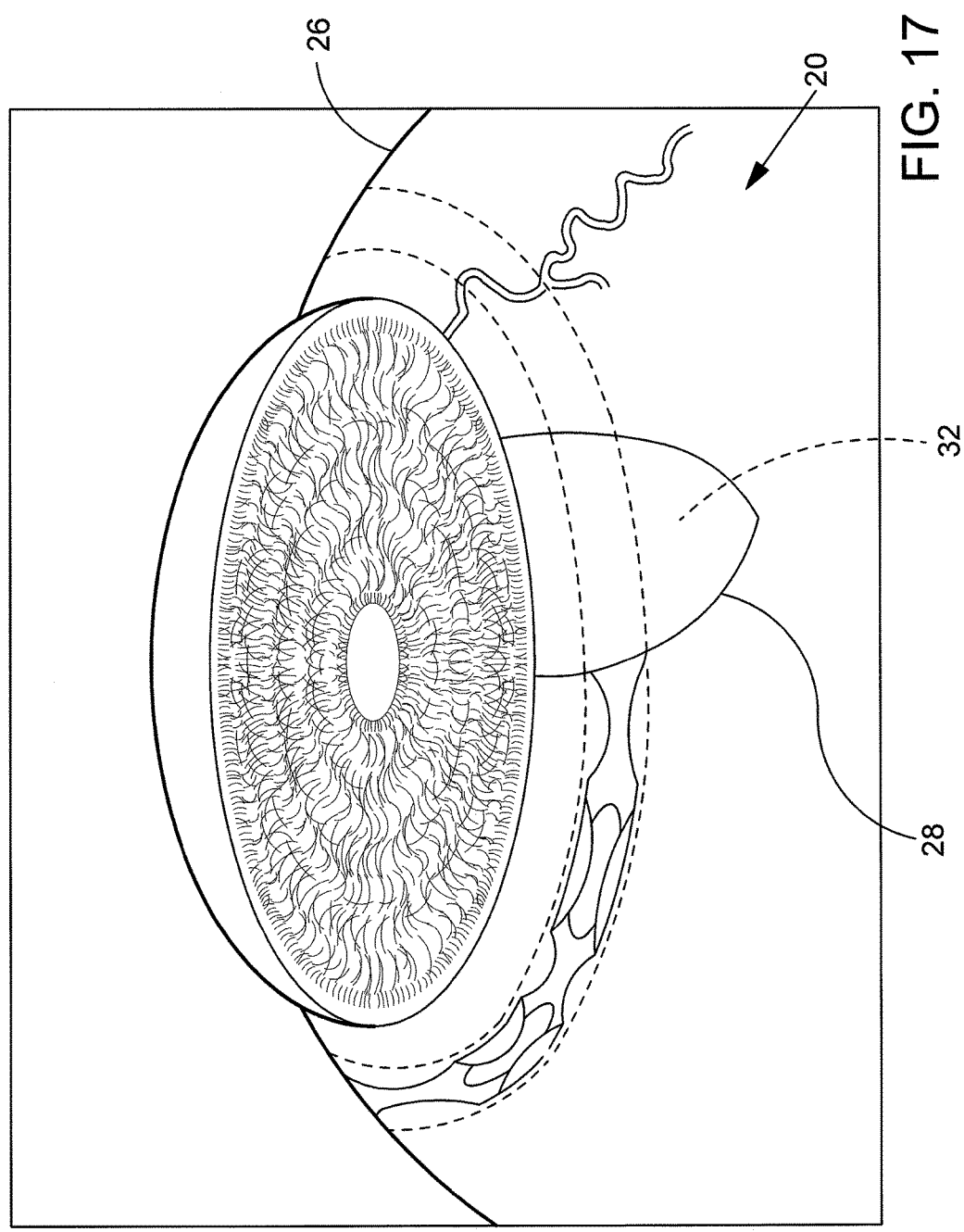
FIG. 17 is a stylized perspective view of the eye of FIGS. 9-16 showing closing of the scleral flap.
Figure 20A:
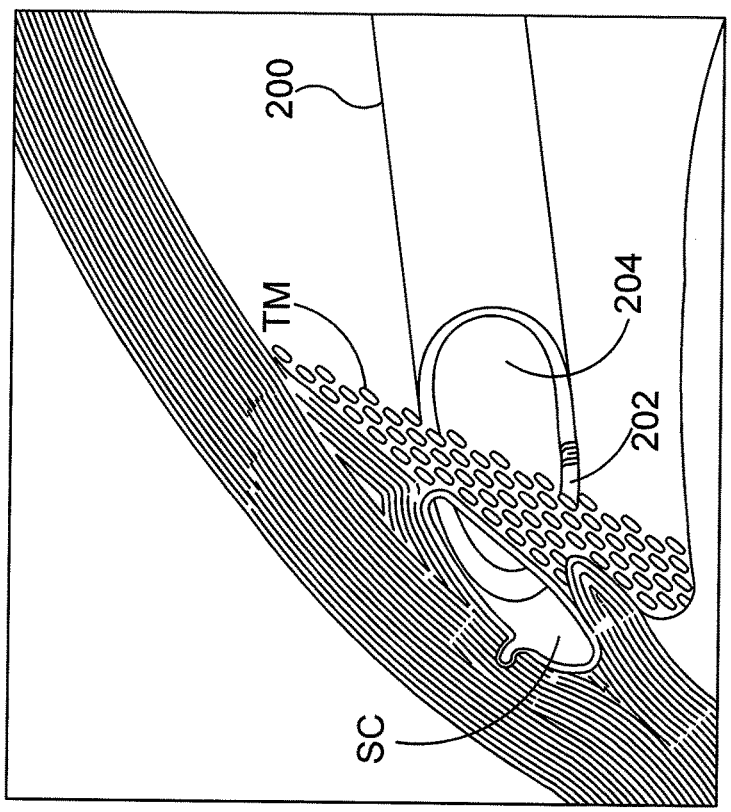
Figure 20B:
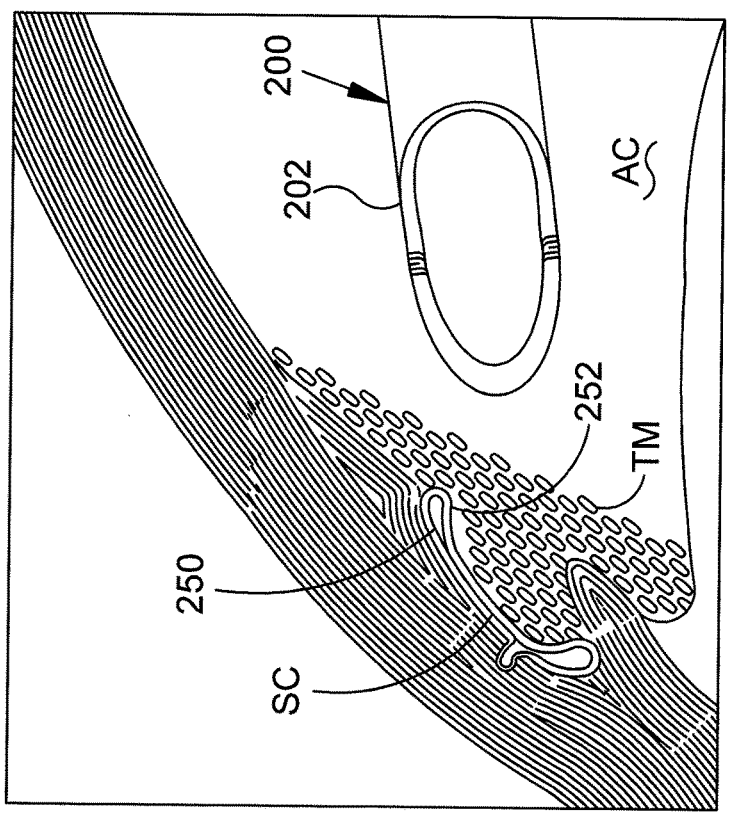

FIG. 17 is an additional perspective view showing a portion of eye 20. In the embodiment of FIG. 17, first scleral flap 28 has been folded over recess 32. In some useful methods, first scleral flap 28 is secured to the remainder of sclera 26 with a plurality of sutures.

FIG. 18A and FIG. 18B are stylized plan views showing an eye 20. A recess 32 has been formed in eye 20. In the embodiment of FIG. 18A, a single aqueous humor drainage device 122A has been advanced through a first opening 36 defined by the wall of Schlemm's canal of eye 20. In the embodiment of FIG. 18B, a first aqueous humor drainage device 122A has been advanced through a first opening 36 defined by the wall of Schlemm's canal and a second aqueous humor drainage device 122B has been advanced through a second opening 38 defined by the wall of Schlemm's canal. The implants shown in FIGS. 18A and 18B may be implanted according to the methods, and using the systems, described above.

FIG. 19A and FIG. 19B are stylized plan views showing an eye 20. A recess 32 has been formed in eye 20. A first aqueous humor drainage device 122 has been advanced into Schlemm's canal of first eye 20. In the exemplary embodiment of FIG. 19A, an inlet portion 46 of first aqueous humor drainage device 122 has been positioned to extend into the anterior chamber AC of first eye 20. The aqueous humor drainage device 122 in FIG. 19B, on the other hand, lies entirely within Schlemm's canal and does not extend into the anterior chamber AC of eye 20. Methods in accordance with this detailed description may include the step of advancing an inlet portion of a first aqueous humor drainage device into the anterior chamber of an eye. The implants shown in FIGS. 19A and 19B may be implanted according to the methods, and using the systems, described above.

The methods illustrated in FIGS. 9-19 may be generally referred to as ab externo methods. Access to Schlemm's canal may be established using an ab interno approach or an ab externo approach. The ab externo methods described herein may be particularly useful when treating closed angle forms of glaucoma. Methods in accordance with this detailed description may include the steps of identifying a patient suffering from closed angle glaucoma and performing the method steps illustrated herein on the eye(s) of that patient. In some embodiments, a substantially straight cannula (having, e.g., a blunt distal tip) is used in connection with ab externo approaches.

Figure 21:
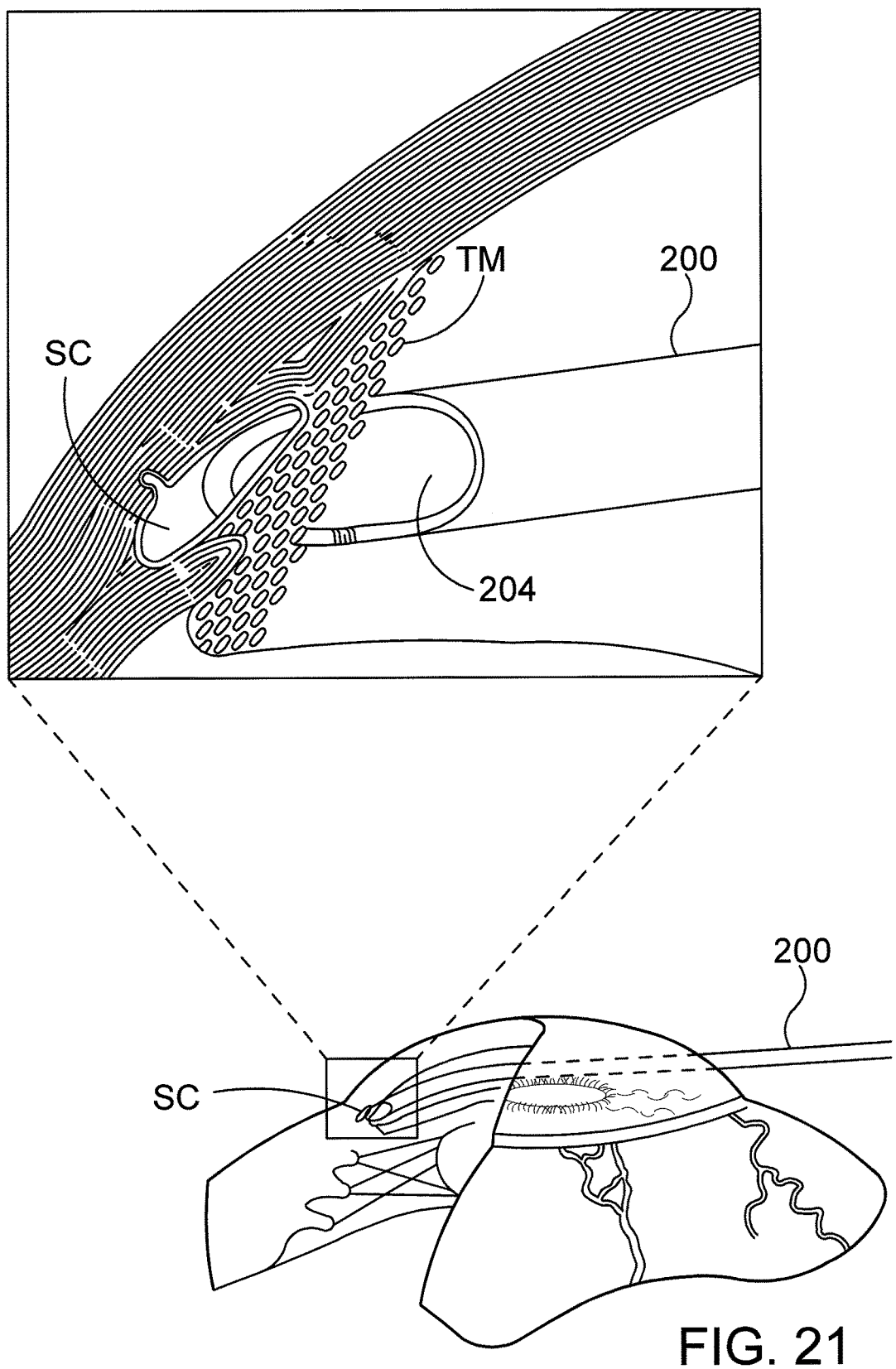

FIGS. 2 and 20-22 show the use of an ab interno approach to deliver a channel tool and/or ocular implant according to embodiments of this invention. FIG. 20A shows a distal tip 202 of a delivery system cannula 200 passing through the anterior chamber AC of an eye. In this view, the inner major wall 252 of Schlemm's canal SC in apposition with the outer major wall 250 preventing circumferential flow within the canal and eliminating a flow path for aqueous access with the closest collector channel. In FIG. 20B, the distal tip 202 of cannula 200 has passed through the trabecular meshwork TM so that at least a portion of a distal opening 204 of cannula 200 is within Schlemm's canal SC. In FIG. 20C, a channel tool 226 is being advanced through distal opening 204 of cannula 200 into Schlemm's canal to determine whether that portion of Schlemm's canal provides a suitable location for the delivery of an ocular implant and/or to open that portion of Schlemm's canal, either through the mechanical action of the advancing channel tool, via the injection of a fluid such as viscoelastic, or both. FIG. 20C includes a plurality of arrows representing fluid flowing through the side walls of channel tool 226. This fluid may be injected into Schlemm's canal in a series of controlled-volume increments to gently separate the walls of the canal in areas where Schlemm's canal is obstructed. Thereafter, an ocular implant (not shown) may be placed in that portion of Schlemm's canal before withdrawing the cannula 200 from Schlemm's canal, as shown in FIG. 20D. FIG. 21 shows cannula 200 entering through the cornea of the eye into the anterior chamber and Schlemm's canal.

Figure 22A:
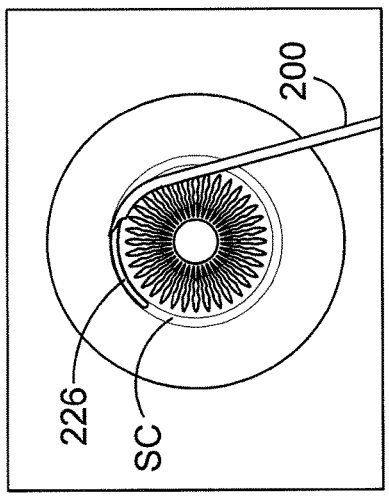
FIGS. 22A-F show details of a method of using the system of this invention.
Figure 22B:
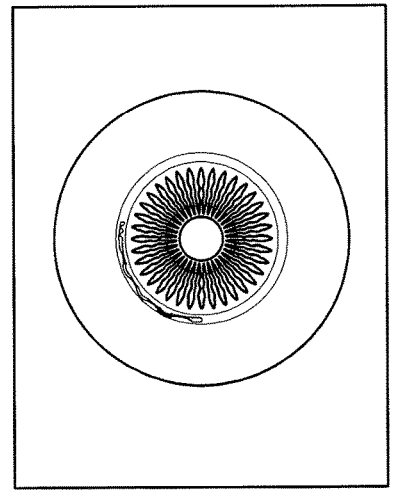
Figure 22C:
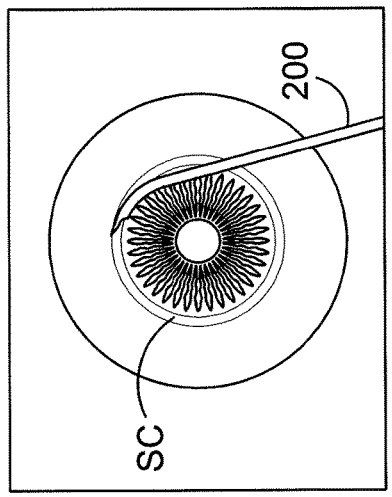
Figure 22D:
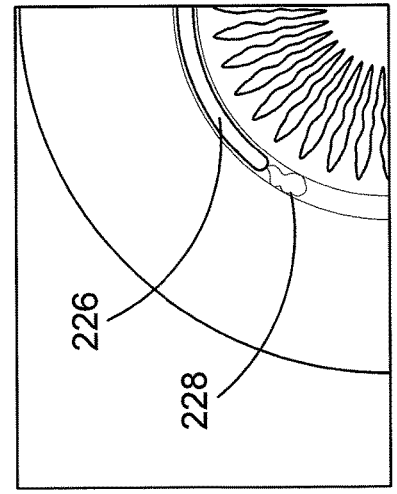
Figure 22E:
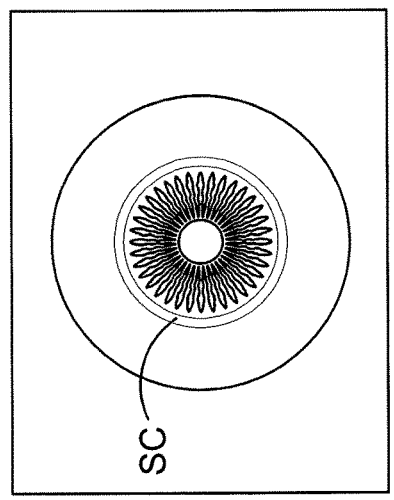
Figure 22F:
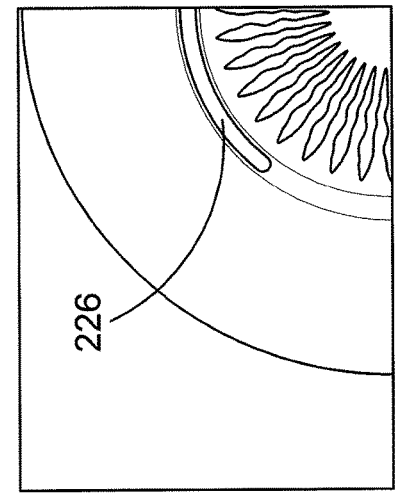

FIGS. 22A-F show steps of a therapy method according to this invention. In FIG. 22B, a cannula 200 has been inserted through the anterior chamber of the eye to place the distal tip 202 at least partially in Schlemm's canal SC. In FIGS. 22C and 22D, a channel tool 226 has been advanced out of cannula 200 into Schlemm's canal SC. A fluid 228 such as viscoelastic may be ejected from channel tool 226 into Schlemm's canal to provide lubrication for the advancement of channel tool 226 and/or to dilate Schlemm's canal. An ocular implant 250 may thereafter be placed in Schlemm's canal, as shown in FIG. 22F.

In some cases, a visible colorant may be added to the viscoelastic composition. When this is the case, the visible colorant may facilitate and evaluation of canal patency. The information gained during this may assist a physician in pre-screening a patient and predicting the potential success of an aqueous drainage aqueous humor drainage device placement procedure for that patient.

FIG. 23A is a stylized perspective view illustrating an exemplary therapy system 3100 in accordance with this detailed description. FIG. 23B is an enlarged detail view further illustrating a portion of therapy system 3100. FIG. 23A and FIG. 23B will be collectively referred to as FIG. 23. The therapy system 3100 of FIG. 23 includes an ocular implant 3122, a channel tool 3152, a push tube 3190, a cannula 3108, and a fluid injection assembly 3162. Therapy system 3100 of FIG. 23 may be used, for example, to determine whether Schlemm's canal of an eye provides a suitable location for the delivery of ocular implant 3122, to open Schlemm's canal of the eye, and/or to place an ocular implant in Schlemm's canal of the eye.

In the embodiment of FIG. 23, push tube 3190 and ocular implant 3122 are both disposed about channel tool 3152. In FIG. 23B, push tube 3190 can be seen extending through a distal port 3109 of cannula 3108. A distal portion of channel tool 3152 can be seen extending beyond ocular implant 3122 in FIG. 23A. In the embodiment of FIG. 23, channel tool 3152 is slidingly disposed in lumens defined by push tube 3190 and ocular implant 3122. Accordingly, channel tool 3152 is free to translate in axial directions (e.g., distal and proximal directions) with respect to both push tube 3190 and ocular implant 3122. This arrangement allows channel tool 3152 to be advanced beyond ocular implant 3122 and into Schlemm's canal. The distal end of channel tool 3152 may be advanced through a portion of Schlemm's canal, for example, to determine whether that portion of Schlemm's canal provides a suitable location for the delivery of ocular implant 3122. After making this determination, the user may advance ocular implant 3122 into the identified portion of Schlemm's canal. In the exemplary embodiment of FIG. 23, ocular implant 3122 may be advanced using push tube 3190.

The motion of push tube 3190 and channel tool 3152 may be controlled using a proximal control 3102 of therapy system 3100. In the exemplary embodiment of FIG. 23, proximal control 3102 includes a first mechanism 3166A and second mechanism 3166B. First mechanism 3166A is capable of advancing and retracting channel tool 3152. Push tube 3190 may be advanced and retracted in axial directions by a second mechanism 3166B.

Cannula 3108 of therapy system 3100 is adapted and configured to deliver channel tool 3152 and ocular implant 3122 into Schlemm's canal of a human eye. A number of exemplary cannulas that may be used with the therapy systems described herein are disclosed in U.S. patent application Ser. No. 12/632,738. The disclosure of this U.S. patent application is hereby incorporated by reference in its entirety.

Ocular implant 3122 of therapy system 3100 is adapted and configured to be disposed within Schlemm's canal of a human eye. Ocular implants that may be suitable in some applications are disclosed e.g., in U.S. Pat. No. 7,740,604; U.S. Patent Publ. No. 2009/0082860; U.S. Patent Publ. No. 2009/0227934; U.S. Patent Publ. No. 2009/0132040; U.S. Patent Publ. No. 2010/0121342; U.S. Patent Publ. No. 2006/0195187; and U.S. application Ser. No. 12/833,863. The entire disclosure of these U.S. Patents and patent applications is hereby incorporated by reference.

Therapy system 3100 of FIG. 23 includes a fluid injection assembly 3162. Fluid injection assembly 3162 may comprise, for example, a syringe (i.e., a piston disposed in a cylinder) that is filled with fluid. Fluid injection assembly 3162 may also include a mechanism configured to dispense a controlled volume of fluid each time an input element of the mechanism (e.g., a lever) is actuated. Fluid injection assembly 3162 fluidly communicates with channel tool 3152 via an injection tube 3156.

FIG. 24 is an enlarged plan view further illustrating ocular implant 3122, push tube 3190, and cannula 3108. With reference to FIG. 24, it will be appreciated that ocular implant 3122 and push tube 3190 are mechanically coupled to each other at a connection 3192. In the embodiment of FIG. 24, an ear of ocular implant 3192 is received in an aperture defined by push tube 3190. Additionally, an ear of push tube 3190 is received in an aperture defined by ocular implant 3192. Channel tool 3152 extends through connection 3192 in the embodiment of FIG. 24. The presence of channel tool 3152 extending through ocular implant 3122 and push tube 3190 locks these two elements together. An area including connection 3192 is surrounded by a frame F in FIG. 24. This area will be enlarged for purposes of illustration in subsequent figures.

FIG. 25A and FIG. 25B are enlarged perspective views illustrating the connection formed between ocular implant 3122 and push tube 3190. In the embodiment of FIG. 25A, ocular implant 3122 and push tube 3190 are mechanically coupled at a connection 3192. In the embodiment of FIG. 25B, the connection between ocular implant 3122 and push tube 3190 has been broken.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating glaucoma in a human eye comprising:
    inserting a distal exit port of a cannula at least partially into Schlemm's canal of the eye;
    delivering a dye through the cannula into Schlemm's canal;
    identifying obstructions within Schlemm's canal; and
    delivering an ocular implant through the cannula into Schlemm's canal.

2. The method of claim 1 further comprising inserting a tool into the cannula, the step of delivering a dye comprising delivering a dye through the tool.

3. The method of claim 2 further comprising moving the tool and the ocular implant with respect to each other within Schlemm's canal.

4. The method of claim 2 wherein the ocular implant delivering step comprises delivering the ocular implant over the tool.

5. The method of claim 2 further comprising opening a channel in Schlemm's canal with the tool.

6. The method of claim 5 wherein the opening step comprises moving the tool within Schlemm's canal.

7. The method of claim 5 wherein the opening step comprises delivering a fluid through the tool.

8. The method of claim 7 further comprises moving the fluid through an obstruction within Schlemm's canal to increase fluid communication between adjacent segments of Schlemm's canal.

9. The method of claim 7 wherein the fluid comprises a dilatation agent adapted to dilate tissue within the Schlemm's canal portion.

10. The method of claim 7 wherein the fluid comprises a therapeutic agent.

11. The method of claim 1 wherein the ocular implant delivering step and the dye delivering step comprise delivering the dye and the ocular implant without removing the distal exit port of the cannula from the eye.

12. The method of claim 1 wherein the inserting step comprises inserting the distal exit port of the cannula at least partially into Schlemm's canal of the eye through an ab interno approach.

13. The method of claim 1 wherein the inserting step comprises inserting the distal exit port of the cannula at least partially into Schlemm's canal of the eye through an ab externo approach.

14. A method of treating glaucoma in a human eye comprising:
    inserting a distal exit port of a cannula at least partially into Schlemm's canal of the eye;
    injecting a dye through the cannula into Schlemm's canal;
    as the dye is injected into Schlemm's canal, observing movement of the dye within Schlemm's canal to identify obstructions within Schlemm's canal; and
    delivering an ocular implant through the cannula into Schlemm's canal.

15. The method of claim 14 wherein the injecting step and the delivering step are performed without removing the distal exit port of the cannula from the eye.

16. The method of claim 14 wherein the inserting step comprises inserting the distal exit port of the cannula at least partially into Schlemm's canal of the eye through an ab interno approach.

17. The method of claim 14 further comprising inserting a tool into the cannula, the step of injecting a dye comprising injecting a dye through the tool.

18. The method of claim 17 further comprising opening a channel in Schlemm's canal with the tool.

19. The method of claim 18 wherein the opening step comprises moving the tool within Schlemm's canal.

20. The method of claim 18 wherein the opening step comprises delivering a fluid through the tool.

\* \* \* \* \*